US007408026B1

(12) United States Patent
Kent et al.

(10) Patent No.: US 7,408,026 B1
(45) Date of Patent: Aug. 5, 2008

(54) SYNTHESIS OF PROTEINS BY NATIVE CHEMICAL LIGATION

(75) Inventors: Stephen B. H. Kent, San Francisco, CA (US); Tom W. Muir, New York, NY (US); Philip E. Dawson, Solana Beach, CA (US)

(73) Assignee: The Scripps Research Institute, La Jolla, CA (US)

( * ) Notice: Subject to any disclaimer, the term of this patent is extended or adjusted under 35 U.S.C. 154(b) by 1067 days.

(21) Appl. No.: 09/710,633

(22) Filed: Nov. 8, 2000

Related U.S. Application Data

(63) Continuation of application No. 08/945,997, filed on Feb. 12, 1998, now Pat. No. 6,184,344.

(51) Int. Cl.
C07K 1/02 (2006.01)
C07K 1/107 (2006.01)
C07K 14/435 (2006.01)
C07K 14/52 (2006.01)

(52) U.S. Cl. .................. 530/323; 530/339; 530/351
(58) Field of Classification Search ................ 558/253, 558/254; 525/54.1, 54.11; 530/816, 323, 530/333, 334, 338, 339, 351; 424/85.1, 85.2, 424/85.4, 85.5, 85.6, 85.7
See application file for complete search history.

(56) References Cited

U.S. PATENT DOCUMENTS

| 4,751,077 | A | * | 6/1988 | Bell et al. .................. 530/351 |
| 4,910,222 | A |   | 3/1990 | Puricelli ..................... 514/513 |
| 4,990,455 | A | * | 2/1991 | Yamagishi et al. .......... 435/69.5 |
| 5,166,322 | A | * | 11/1992 | Shaw et al. ................. 530/351 |
| 6,184,344 | B1 | * | 2/2001 | Kent et al. .................. 530/323 |
| 6,326,468 | B1 | * | 12/2001 | Canne et al. ................ 530/333 |

FOREIGN PATENT DOCUMENTS

WO             96/34878       * 11/1996

OTHER PUBLICATIONS

Baca, et al., "Chemical Ligation of Cysteine-Containing Peptides: Synthesis of a 22 kDa Tethered Dimer of HIV-1 Protease", *J. Am. Chem. Soc. 117*: 1811-1887 (1995).
Canne, et al., "Total Chemical Synthesis of a Unique Transcription Factor-Related Protein: cMyc-Max", *J. Am. Chem. Soc. 117*: 2998-3007.
Canne, et al., "A General Method for the Synthesis of Thioester Resin Linkers for Use in the Solid Phase Synthesis of Peptide-α-Thioacids", *Tetrahedron Letters 36* (8): 1217-1220 (1995).
Clark-Lewis, et al., "Chemical Synthesis, Purication, and Characterization of Two Inflammatory Proteins, Neutrophil Activating Peptide 1 (Interleukin-8) and Neutrophil Activating Peptide 2", *Biochemistry 30* 3128-3135 (1991).
Clark-Lewis, et al., "Structural Requirements for Interleukin-8 Function Identified by Design of Analogs and CXC Chemokine Hybrids", *The Journal of Biological Chemistry 269* (23): 16075-16081 (1994).
D'Andrea, et al., "A Mutation of the Common Receptor Subunit for Interleukin-3 (IL-3), Granulocyte-Macrophage Colony-Stimulating Factor, and IL-5 That Leads to Ligand Independence and Tumorigenicity", *Blood 83* (10): 2802-2808 (1994).
Dawson, et al., "Synthesis of Proteins by Native Chemical Ligation", *Science 266*: 776-779 (1994).
Yamashiro, et al., "New segment synthesis of α-inhibin-92 by the acyl disulfide method", *Int. J. Peptide Protein Res. 31*: 322-334 (1988).
Schnölzer, et al., "In situ neutralization in Boc-chemistry solid phase peptide synthesis", *Int. J. Peptide Res. 40*: 180-193 (1992).
Wieland, et al., "Synthesen einiger β-Indolacetylaminosauren und peptide", *Liebigs. Ann. Chem. 591*: 192-199 (1955).
Offord, "Chemical Approaches to Protein Engineering" in *"Protein Design and the Development of New Therapeutics and Vaccines"*, Hooke, J. B.; Poste, G., Eds.: Plenum Press, 1990, pp. 253-282.
Abrahmsén, et al., "Engineering Subtilisin and Its Substrates for Efficient Ligation of Peptide Bonds in Aqueous Solution", *Biochemistry 30*: 4151-4159 (1991).
Schnölzer, et al., "Constructing Proteins by Dovetailing Unprotected Synthetic Peptides: Backbone-Engineered HIV Protease", *Science 256*: 221-225 (1992).
Muir, et al., "The chemical synthesis of proteins", *Curr. Opin. Biotech. 4*: 420-427 (1993).
Chang, et al., "Subtiligase: A tool for semisynthesis of proteins", *Proc. Natl. Acad. Sci. USA 91*: 12544-12548 (1994).
Tam, et al., "Peptide synthesis using unprotected peptides through orthogonal coupling methods", *Proc. Natl. Acad. Sci. USA 92*: 12485-12489 (1995).
Canne, et al., "Extending the Applicability of Native Chemical Ligation", *J. Am. Chem. Soc. 118*: 5891-5896 (1996).

* cited by examiner

*Primary Examiner*—Jeffrey E Russel
(74) *Attorney, Agent, or Firm*—Donald G. Lewis; Thomas Fitting

(57) ABSTRACT

Proteins of moderate size having native peptide backbones are produced by a method of native chemical ligation. Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full length ligation products are chemically identical to proteins produced by cell free synthesis. Full length ligation products may be refolded and/or oxidized, as allowed, to form native disulfide-containing protein molecules. The technique of native chemical ligation is employable for chemically synthesizing full length proteins.

12 Claims, 10 Drawing Sheets

SYNTHESIS OF PROTEINS BY NATIVE CHEMICAL LIGATION

CROSS-REFERENCE TO RELATED APPLICATION

The present application is a continuation application of and claims priority, under 35 U.S.C. § 120, from U.S. patent application Ser. No. 08/945,997, filed Feb. 12, 1998, which issued on Feb. 6, 2001 as U.S. Pat. No. 6,184,344, and which was a national stage application under 35 U.S.C. § 371 of International Application No. PCT/US95/05668, filed May 4, 1995, which International Application was published in English.

GOVERNMENT RIGHTS

The invention disclosed herein was supported in part by Grants Number R01 GM 48897 and P01 GM 48870 from the National Institutes of Health. The United States government may have certain rights to this invention.

FIELD OF INVENTION

The invention relates to methods and intermediates for chemically ligating two oligopeptides end to end with an amide bond. More particularly, the invention relates to methods and intermediates for chemically ligating oligopeptides wherein an unoxidized N-terminal cysteine of a first oligopeptide condenses with a C-terminal thioester of a second oligopeptide to form a β-aminothioester intermediate which spontaneously rearranges intramolecularly to form an amide bond and the ligation product.

BACKGROUND

Proteins may be synthesized chemically, ribosomally in a cell free system, or ribosomally within a cell. Advances in each of these areas have significantly improved access to many proteins but have also stimulated demand for yet further improvements.

Proteins owe their diverse properties to the precisely folded three dimensional structures of their polypeptide chains. The three dimensional structure of a protein determines its functional attributes. However, at present, it is difficult to predict and/or fully explain the biological properties of a protein from its three dimensional structure alone. A better understanding of how structure determines the biological properties of a protein can be achieved by systematically varying the covalent structure of the molecule and correlating the effects with the folded structure and biological function. Accordingly, there is an increased demand for enhanced synthetic techniques for synthesizing new proteins and protein analogs.

Techniques derived from recombinant DNA-based molecular biology can be employed to facilitate the expression of proteins in genetically engineered microorganisms. The use of site-directed mutagenesis, as disclosed by M. Smith (*Angew. Chem. Int. Ed. Engl.* (1994): vol. 33, p 1214), enables the preparation of large numbers of modified proteins in useful amounts for systematic study, e.g., C. Eigenbrot and A. Kossiakoff, *Current Opinion in Biotechnology* (1992): vol. 3, p 333. The use of innovative approaches increases the range of amino acids that can be incorporated in expression systems and promises to significantly extend the utility of biosynthetic modification of the covalent structure of proteins. (C. J. Noren et al., *Science* (1989): vol. 244, p 182 (1989); J. A. Ellman et al., *Science* (1992): vol. 255, p 197.) However, there appear to be limitations inherent to the nature of ribosomal protein synthesis. (V. W. Cornish, et al., *Proc. Natl. Acad. Sci. USA* (1994): vol. 91, p 2910.)

Chemical synthesis of proteins has also contributed to the exploration of the relationship of protein structure to function. Stepwise solid phase synthesis has permitted the de novo preparation of small proteins. (T. W. Muir et al., *Curr. Opin. Biotech.* (1993): vol. 4, p 420.) There are also several examples of the use of stepwise solid phase synthesis of whole proteins to explore the molecular basis of biological function. (M. Miller, et al., *Science* (1989): vol. 246, p 1149; A. Wlodawer, et al., *Science* (1989): vol. 245, p 616; L. H. Huang, et al., *Biochemistry* (1991): vol. 30, p 7402; and K. Rajarathnam, et al., *Science* (1994): vol. 264, p 90.)

Semi-synthesis through the conformationally-assisted religation of peptide fragments can also be employed, in special instances, to study of the structure/function relationship of proteins. (R. E. Offord, "Chemical Approaches to Protein Engineering", in *Protein Design and the Development of New therapeutics and Vaccines*, J. B. Hook, G. Poste, Eds., (Plenum Press, New York, 1990) pp. 253-282; C. J. A. Wallace, et al., *J. Biol. Chem.* (1992): vol. 267, p 3852. An important extension of the semisynthesis approach is the use of enzymatic ligation of cloned or synthetic peptide segments. (L. Abrahmsen, et al., *Biochemistry* (1991): vol. 30, p 4151; T. K. Chang, et al., *Proc. Natl. Acad. Sci. USA* (1994): in press.) Although the above methodologies have been successfully applied to the synthesis of proteins and protein analogs, T. W. Muir et al., report that there is a continued interest in the wider application of the tools of organic chemistry to the study of proteins (*Curr. Opin. Biotech.* (1993): vol. 4, p 420.)

Stephen Kent et al. recently introduced the chemical ligation of unprotected peptide segments as an improved route to the total synthesis of proteins. (M. Schnlzer, et al., *Science* (1992): vol., 3256, p 221.) Chemical ligation involves the chemoselective reaction of unprotected peptides to give a product with an unnatural backbone structure at the ligation site. Use of unprotected peptides circumvented the difficulties inherent to classical chemical synthesis, viz complex combinations of protecting groups that lead to limited solubility of many synthetic inter-mediates, e.g. K. Akaji, et al., *Chem. Pharm. Bull.* (Tokyo) (1985): vol. 33, p 184. In contrast, the chemical ligation technique has allowed us to make good use of the ability to routinely make, purify, and characterize unprotected peptides 50 or more residues in length. Using optimized stepwise solid phase methods the preparation in good yield and high purity of peptides up to 60 residues is routine. In favorable cases, peptides of 80+ residues can be prepared. (M. Schnolzer, et al., *Int. J. Pept. Prot. Res.* (1992): vol. 40, p 180-193.)

The key aspect of the above approach to chemical ligation is the use of a chemoselective reaction to specifically and unambiguously join peptides by formation of an unnatural (i.e. non-peptide) backbone structure at the ligation site. It has permitted the facile preparation of a wide range of backbone-modified proteins, including analogues of protein domains, e.g., ligated 10F3, the integrin-binding module of fibronectin: 95 residues (M. Williams, et al., *J. Am. Chem. Soc.* (1994): in press.) The catalytic contribution of flap-substrate hydrogen bonds in HIV-1 protease has been elucidated by the chemical synthesis of a homodimer of 99 residue subunits of this protein by chemical ligation. (M. Baca, et al., *Proc. Natl. Acad. Sci. U.S.*, (1993): vol. 90, p 11638.) Chemical ligation has also proven to be useful for the routine, reproducible synthesis of large amounts of proteins in high purity with full biological activity (20). (R. C. deLisle Milton, et al., "Synthesis of Proteins by Chemical Ligation of Unprotected Peptide Segments: Mirror-Image Enzyme Molecules, D- & L-HIV Protease Analogs," in *Techniques in Protein Chemistry IV*, Academic Press, New York, pp. 257-267 (1992).)

Chemical ligation can also be employed for the straightforward production of protein-like molecules of unusual topology, e.g., four-helix bundle template-assembled synthetic protein (MW 6647 Da) (P. E. Dawson, et al., *J. Am. Chem. Soc.* (1993): vol. 115, p 7263); homogeneous multivalent artificial protein (MW 19,916 Da) (K. Rose, *J. Am. Chem. Soc.* (1994): vol. 3116, p 30); artificial neoprotein mimic of the cytoplasmic domains of a multichain integrin receptor (MW 14,194 Da) (T. W. Muir, et al., *Biochemistry*, (1994): vol. 33, pp 7701-7708; and peptide dendrimer (MW 24,205 Da) (C. Rao, et al., *J. Am. Chem. Soc.* (1994): vol. 116, p 6975. The range of proteins accessible by this technique is limited by the size of the synthetic peptide segments.

A useful extension would occur if one had direct synthetic access to native backbone polypeptide chains up to the size of typical protein domains. (A. L. Berman, et al., *Proc. Natl. Acad. Sci. USA* (1994): vol. 91, p 4044.) Chemical ligation would then be employed to string these domains together to explore the world of proteins in a general fashion.

A modular strategy for the total synthesis of proteins has been developed, based on the convergent chemical ligation of unprotected peptides has been disclosed by L. E. Canne, et al. (presented at the Annual Meeting of the Protein Society, San Diego, July 1994). Protein domains (modules) were prepared by chemical ligation of 50-70 residue segments; these domains were then stitched together to give the target protein. Mutually compatible ligation chemistries are required: intradomain ligation should optimally yield a stable, peptide-like bond; inter-domain ligation will tolerate a wider variation of properties of the structure formed at the ligation site.

Straightforward total chemical synthesis of proteins represents the realization of an important objective of organic chemistry. It raises the exciting prospect of unrestricted variation of protein covalent structure made possible by general synthetic access, and will give new impetus to exploration of the structural basis of properties such as folding, stability, catalytic activity, binding, and biological action.

What is needed is a technique of native chemical ligation which combines the formation of a native peptide bond at the ligation site with the advantages of chemoselective reaction of unprotected peptides. This second generation ligation chemistry would significantly increase the size of native backbone polypeptides directly accessible by total chemical synthesis. It could be usefully applied to a wide range of synthetic targets, including proteins of moderate size, and it allows direct access to protein functional domains. Native chemical ligation is a foundation stone of a general modular approach to the total chemical synthesis of proteins. Furthermore, it is compatible with the use of both chemically synthesized peptides and peptide segments derived from other sources.

SUMMARY

One aspect of the invention is directed to a method of native chemical ligation. The method of native chemical ligation facilitates the chemical synthesis of proteins and large oligopeptide. The principle of 'native chemical ligation' is shown in FIG. 1. The first step is the chemoselective reaction of an unprotected synthetic peptide-α-thioester with another unprotected peptide segment containing an N-terminal Cys residue, to give a thioester-linked intermediate as the initial covalent product. Without change in the reaction conditions, this intermediate undergoes spontaneous, rapid intramolecular reaction to form a native peptide bond at the ligation site. The target full length polypeptide product is obtained in the desired final form without further manipulation. The general synthetic access provided by the method of native chemical ligation greatly expands the scope of variation of the covalent structure of the protein molecule.

One embodiment of the invention provides a method for ligating a first oligopeptide with a second oligopeptide end to end for producing an oligopeptide product. The first and second oligopeptides are admixed in a reaction solution including a catalytic thiol. The catalytic thiol may be an unconjugated mercaptan or a conjugated thiol. Preferred catalytic thiols include benzyl mercaptan, thiophenol, 1-thio-2-nitrophenol, 2-thio-benzoic acid, 2-thio-pyridine, 4-thio-2-pyridinecarboxylic acid, and 4-thio-2-nitro-pyridine. The first oligopeptide includes a C-terminal thioester. The second oligopeptide includes an N-terminal cysteine having an unoxidized sulfhydryl side chain. The unoxidized sulfhydryl side chain of the N-terminal cysteine is then condensed with the C-terminal thioester to produce an intermediate oligopeptide which links the first and second oligopeptides with a β-aminothioester bond. The β-aminothioester bond of the intermediate oligopeptide then undergoes an intramolecular rearrangement to produce the oligopeptide product which links the first and second oligopeptides with an amide bond.

Another aspect of the invention is directed to an oligopeptide intermediate which comprises a first oligopeptide segment having a C-terminal thioester, a second oligopeptide segment having a N-terminal cysteine, and a β-aminothioester linkage unit which links the C-terminal thioester and the N-terminal cysteine. The β-aminothioester linkage unit spontaneously rearranges intramolecularly to form an amide bond linking the first and second oligopeptides segments end to end.

Another aspect of the invention is directed to a method for producing an oligopeptide having a C-terminal thioester. The method admixes a resin having a linker with an unoxidized thiol with a Boc-amino acid succinimide ester under reaction conditions to produce a Boc-amino thioester-resin. An oligopeptide is then assembled onto the Boc-amino thioester-resin by stepwise solid phase peptide synthesis. When the oligopeptide is complete, the Boc-amino thioester-resin is cleaved with HS to produce an oligopeptide having a C-terminal thiol. The C-terminal thiol is then converted to an oligopeptide having a C-terminal thioester.

The oligopeptide thioester (α-COSR moiety) of FIG. 1 can be readily generated from a corresponding oligopeptide thiol (αCOSH) prepared by highly optimized stepwise SPPS on a thioester resin. The thioester resin was prepared by the method of L. E. Canne et al., Tetrahedron Letters (1995): vol. 36, pp. 1217-1220, incorporated herein by reference. The method of Canne employs the thioester resin disclosed by Blake and Yamashiro (J. Blake, Int. J. Pept. Protein Res. (1981): vol. 17, p 273; D. Yamashiro, et al., Int. J. Pept. Protein Res. (1988): vol. 31, p 322). Peptide products were cleaved, purified, and characterized by conventional methods. (M. Schnolzer, et al., Int. J. Pept. Protein Res., (1992): vol. 40, pp 180-193.)

The Yamashiro methodology activates a thiocarboxyl group on a protected oligopeptide with diaryl disulfides to give acyl disulfides (Yamashiro et. al. *Int. J. Peptide Protein Res.* (1922): vol. 31, pp 322-334). These C-terminal-peptide-acyl-disulfides are highly reactive electrophilic intermediates which are attacked and subsequently coupled with an α-amino group on the N-terminus of a second peptide to form native peptide bonds. The reported coupling yields using 2,2'-dipyridyl disulfide as the activator of the thiocarboxyl group afford the desired α-IB-92 product in 45% yield. Overall yields based on the starting resin for a 3-segment synthesis of α-IB-92 are reported as 8%, while a 2-segment synthesis gave 11%.

Due to the high reactivity of the diaryl disulfide bond, the Yamashiro approach requires extensive protection and deprotection of amino acid residues present in the peptide molecule. The lysine group for example is protected as a citraconyl derivative because of the reactive amine functionality. Additionally, an Msc group or tBOC group is used to protect any terminal amine functionalities present in the molecule.

The invention stated herein does not require the use of any protecting groups for the coupling of two oligopeptides because a less reactive (and thus more chemoselective) thioester electrophile is used instead of the acyl disulfide moiety (Yamashiro's approach). In the intermolecular coupling step, this thioester electrophile requires a more nucleophilic sulfhydryl moiety rather than a free amine. The nucleophilic sulfhydryl moiety can be found on cysteine residues. Since the amino and hydroxyl functionalities are relatively unreactive to the thioester electrophile, a selective coupling of the two unprotected oligopeptides is achieved with the cysteine sulfhydryl moiety. The sulfhydryl group on the cysteine of peptide 2 will first attack the thioester of peptide 1 and form a coupled thioester intermediate. This coupled thioester intermediate is concomitantly attacked by the free α-amino moiety from the cysteine and spontaneously rearranges to form the native peptide bond. Yields are therefore increased by eliminating protection and deprotection steps, since side undesired reactions are reduced (FIG. 1).

The thioester moiety is prepared from a precursor thioacid which is obtained by optimized stepwise solid-phase peptide synthesis on a aminomethyl resin support equipped with a thioester resin linker. The precursor thioacid is subsequently generated in liquid HF at 0° C. in 1 hour (Yamashiro et. al. *Int. J. Pept. Protein Res.* (1988): vol. 31, p 322).

A procedure for the synthesis of the thioester linker with use of a stepwise solid phase peptide synthesis has been reported by Blake (Blake et. al. *Proc. Natl. Acad. Sci. USA* (1981): vol. 78, 4055) and Yamashiro (Yamashiro et. al. *Int. J. Pept. Protein Res.* (1988): vol. 31, p 322). This method is undesirable, however, because it requires the conversion of Boc-amino acid succinimide esters to the corresponding Boc-amino thioacids with hydrogen sulfide. An improved methodology reported herein, utilizes the Boc-amino acid succinimide ester directly and therefore avoids the inconvenience and hazards of hydrogen sulfide gas (Kent et. al. *Tetrahedron Lett.* (1995): vol. 36, p 1217).

In this method (FIG. 2), thiol 3 is generated from the reaction of chloride 2 (Yamashiro et. al. Int. J. Pept. Protein Res. (1988): vol. 31, p 322) with thiourea, followed by hydrolysis of the resulting thiouronium salt in aqueous base. Thiol 3 is a general intermediate which can be reacted with a wide range of commercially available Boc-amino acid succinimide esters to produce the desired thioester linker 1 which is conveniently isolated as the dicyclohexylamine (DCHA) salt.

Model studies were undertaken with small peptides to investigate the native chemical ligation approach. To help explore the mechanism of the reaction, the peptide Leu-Tyr-Arg-Ala-Gly-α-COSBzl (SEQ ID NO 3) was reacted with Ac-Cys. The exact mass of the resulting ligation product was determined by electrospray mass spectrometry, and was consistent with a thioester-linked peptide as the ligation product generated by nucleophilic attack of the Ac-Cys side chain on the α-thioester moiety of the peptide. Reaction of Leu-Tyr-Arg-Ala-Gly-α-COSBzl (SEQ ID NO 3) with H-Cys-Arg-Ala-Glu-Tyr-Ser (SEQ ID NO 2) (containing an unblocked α-NH$_2$ functional group) proceeded rapidly at pH 6.8 (below pH 6 the reaction proceeded very slowly, suggesting the involvement of the ionized thiolate form of the Cys side chain), and gave a single product of the expected mass. This product lacked susceptibility to nucleophiles, and had the ability to form disulfide-linked dimeric peptides, indicating unambiguously the formation of a native amide bond at the ligation site. These studies were consistent with the mechanism shown in FIG. 1, in which the initial thioester ligation product was not observed as a discrete intermediate because of the rapid rearrangement to form a stable peptide bond. Facile intramolecular reaction results from the favorable geometric arrangement of the α-NH$_2$ moiety with respect to the thioester formed in the initial chemoselective ligation reaction. Use of such 'entropy activation' for peptide bond formation is based on principles enunciated by Brenner. (M. Brenner, in Peptides. Proceedings of the Eighth European Peptide Symposium H. C. Beyerman, Eds. (North Holland, Amsterdam, 1967) pp. 1-7.) The concept of 'entropy activation' for peptide bond formation has been more recently adopted by D. S. Kemp et al. (J. Org. Chem. (1993): vol. 58, p 2216) and by C.-F. Liu, et al. (J. Am. Chem. Soc. (1994): vol. 116, p 4149).

Several model peptides have been synthesized by the method of native chemical ligation. The successful synthesis of these model peptides establish that native chemical ligation is generally applicable to peptides containing the full range of functional groups normally found in proteins. Even free internal Cys residues may be present in either of the reacting segments. Internal Cys residues can undergo ester exchange with the peptide-a-thioester component; however, this reaction is unproductive because no rearrangement to the amide bond can occur; the thioester formed is readily reversible and remains a productive part of the reacting system. As disclosed herein, native chemical ligation is limited to reaction at an N-terminal Cys residue. It is important to prevent the side chain thiol of this Cys from oxidizing to form a disulfide linked dimer, because this is unreactive in the ligation. An excess of thiol corresponding to the thioester leaving group was used to keep the Cys residues in reduced form without interfering with the ligation reaction. The amino-terminal peptide segment must be prepared by chemical synthesis to equip it with the necessary α-COSR functionality. Furthermore, for optimal ligation, this component should have an unhindered (i.e. non β-branched) C-terminal amino acid. Solubilizing agents such as urea or guanidine hydrochloride did not interfere with the ligation and could be used to enhance the concentration of peptide segments, and thus increase the reaction rate.

Further model reactions demonstrate that the use of better thioester leaving groups results in faster ligation reactions. We applied this observation to the native chemical ligation of peptides from the extracellular domain of a human cytokine receptor (R. D'Andrea, et al., Blood, (1994): vol. 83, p 2802.) as shown in FIG. 5. Use of the 5-thio-2-nitrobenzoic acid (-SNB) leaving group, corresponding to the reduced form of Elman's reagent, gave rapid high yield reaction. As described below in connection with FIG. 5, the reaction between the peptide segments was observed to have gone essentially to completion in less than 5 minutes, giving the 50 residue product with a native peptide bond at the site of ligation. Thus, rapid native chemical ligation can be achieved by use of a thioester leaving group with suitably tuned properties.

Application of the native chemical ligation method to the total synthesis of a protein molecule was illustrated by the preparation of human interleukin 8 (IL-8). (M. Baggiolini, et al., FEBS Lett. (1989): vol. 307, p 97; I. Clark-Lewis, et al., J. Biol. Chem. (1994): vol. 269, p 16075 (1994); I. Clark-Lewis, Biochemistry (1991): vol. 30, p 3128; and K. Rajarathnam, et al., (1994): Biochemistry, (1994): vol. 29, p 1689.) The 72 amino acid polypeptide chain contains four Cys residues, which form two functionally critical disulfide bridges in the native protein molecule. The total synthesis of IL-8 is shown in FIG. 7. The two unprotected synthetic peptide segments reacted cleanly to give the full length polypeptide chain in reduced form without further chemical manipulation (9). This successful ligation was particularly significant because the 33- and 39-residue IL-8 segments each contained two Cys residues, and together encompassed 18 of the 20 genetically encoded amino acids found in proteins. The purified product was folded and oxidized as previously described, to give IL-8 with a mass precisely 4 daltons less than that of the original ligation product, indicating the formation of two disulfide bonds. The properties of this folded product were identical to those of previously studied authentic IL-8 samples. Titration in an assay for neutrophil elastase release demonstrated that the potencies (ED50=0.3 nM) and maximal responses of the folded, ligated [Ala33]IL-8 and the corresponding molecule obtained by conventional synthesis were indistinguishable and identical to native sequence IL-8. This result unambiguously confirmed the formation of a peptide bond at the ligation site, because the thioester-to-amide rearrangement must have taken place to give the free $Cys^{34}$ side chain that formed the native disulfide bond (see FIG. 7).

Proteins are usually studied by expression in genetically engineered micro-organisms using the methods of recombinant DNA-based molecular biology. Methods such as site-directed mutagenesis have had a major impact on the ability to prepare large numbers of modified proteins in useful amounts for systematic study. Innovative approaches have increased the range of amino acids that can be incorporated in expression systems and promise to significantly extend the utility of biosynthetic modification of the covalent structure of proteins. However, there appear to be limitations inherent to the nature of ribosomal protein synthesis.

Wieland discloses a method for synthesizing dipeptides using a thioester intermediate. (Wieland et. al. *Liebigs Ann. Chem.* (1953): vol. 580, p 159.) Wieland utilizes the reaction of S-glycyl-(or other un-branched aminoacyl-) thiophenols with cysteine. Thus, the sulfhydryl group on the cysteine residue first attacks the thioester of the S-glycyl-thiophenol and forms a coupled thioester intermediate. This coupled thioester intermediate is concomitantly attacked by the free α-amino moiety from the cysteine and spontaneously rearranges to form the native peptide bond.

A limitation of the Wieland approach is the size of the molecules utilized (only mono-amino acids are coupled to cysteine) and stems from the methodology used for the synthesis of the thioester. To form the thioester, Wieland's approach requires the activation of the terminal carboxylic acid as a mixed anhydride, acid chloride or thioacid. A problem arises if an acidic moiety is present in an amino acid residue such as Asp(D) and Glu(E). In these cases, the Wieland produces an undesired side reaction and therefore requires a complex protecting group strategy, particularly if oligopeptides are synthesized.

The invention described herein eliminates the need for an elaborate protecting group strategy since the oligopeptide-thioester moiety is derived from a precursor thioacid. This precursor thioacid (peptide-α-COSH) is synthesized by a standard stepwise solid-phase peptide synthesis on an aminomethyl resin support, equipped with a thioester resin linker. The precursor thioacid is cleaved from the linker/resin almost quantitatively (99%) in liquid HF at 0° C. for 1 hour.

The thioester peptide (peptide-α-COSR) can be synthesized in two general ways:

(1) Reaction of a crude lyophilized thioacid peptide (peptide-α-COSH) with Ellman's reagent (5,5'-dithiobis-2-nitrobenzoic acid, available from Aldrich company) at pH 5.5 (2.0 equivalents), 6M Guanidine in 100 mM Na acetate buffer. This gives the SNB-thioester peptide (peptide-α-COSNB) which is subsequently purified by reversed phase high performance liquid chromatography (RPHPLC).

(2) Reaction of a crude lyophilized thioacid peptide (peptide-α-COSH) with benzyl bromide at pH 4.0, 6M guanidine and 100 mM Na acetate buffer. The benzyl thioester (peptide-α-COSBn) is then purified by RPHPLC.

The conditions stated above, permit the formation of an unprotected oligonucleotide which is equipped with the activated thioester. Subsequent reaction with a second peptide containing a terminal cysteine residue, permits a facile coupling with the formation of a native peptide bond and can generate oligopeptide chains of 100 or more amino acid residues (FIG. 1).

In favorable cases, chemical synthesis has already made important contributions to the exploration of the relationship of protein structure to function. Stepwise solid phase synthesis has permitted the de novo preparation of small proteins (14) and there have been several notable examples of the use of this method of total protein synthesis to explore the molecular basis of biological function. Another method that has in special instances allowed chemistry to be applied to the study of proteins is semi-synthesis through the conformationally-assisted religation of peptide fragments. An important extension of the semisynthesis approach is the use of enzymatic ligation of cloned or synthetic peptide segments. Although these methods currently have severe limitations, there continues to be serious interest in the wider application of the tools of organic chemistry to the study of proteins.

Native chemical ligation provides precisely that capability. It combines the formation of a native peptide bond at the ligation site with the advantages of chemoselective reaction of unprotected peptides. This second generation ligation chemistry dramatically increases the size of native backbone polypeptides directly accessible by total chemical synthesis. It can be usefully applied to a wide range of synthetic targets, including proteins of moderate size, and it allows direct access to protein functional domains. Native chemical ligation is a foundation stone of a general modular approach to the total chemical synthesis of proteins. Furthermore, it is compatible with the use of both chemically synthesized peptides and peptide segments derived from other sources.

Straightforward total chemical synthesis of proteins represents the realization of an important objective of organic chemistry. It provides for unrestricted variation of protein covalent structure made possible by general synthetic access, and provides new impetus to exploration of the structural basis of properties such as folding, stability, catalytic activity, binding, and biological action.

In an alternative embodiment, the carboxy-terminal peptide segment or protein module can be expressed by standard recDNA means; provided the product contained an N-terminal Cys residue, it could be reacted with the synthetic amino-terminal peptide-α-COSR using the native chemical ligation described here to give a product in which part of the protein had derived from chemical synthesis and part from ribosomal synthesis.

DETAILED DESCRIPTION

Peptide-α-Thioacid Formation

Figure 1:
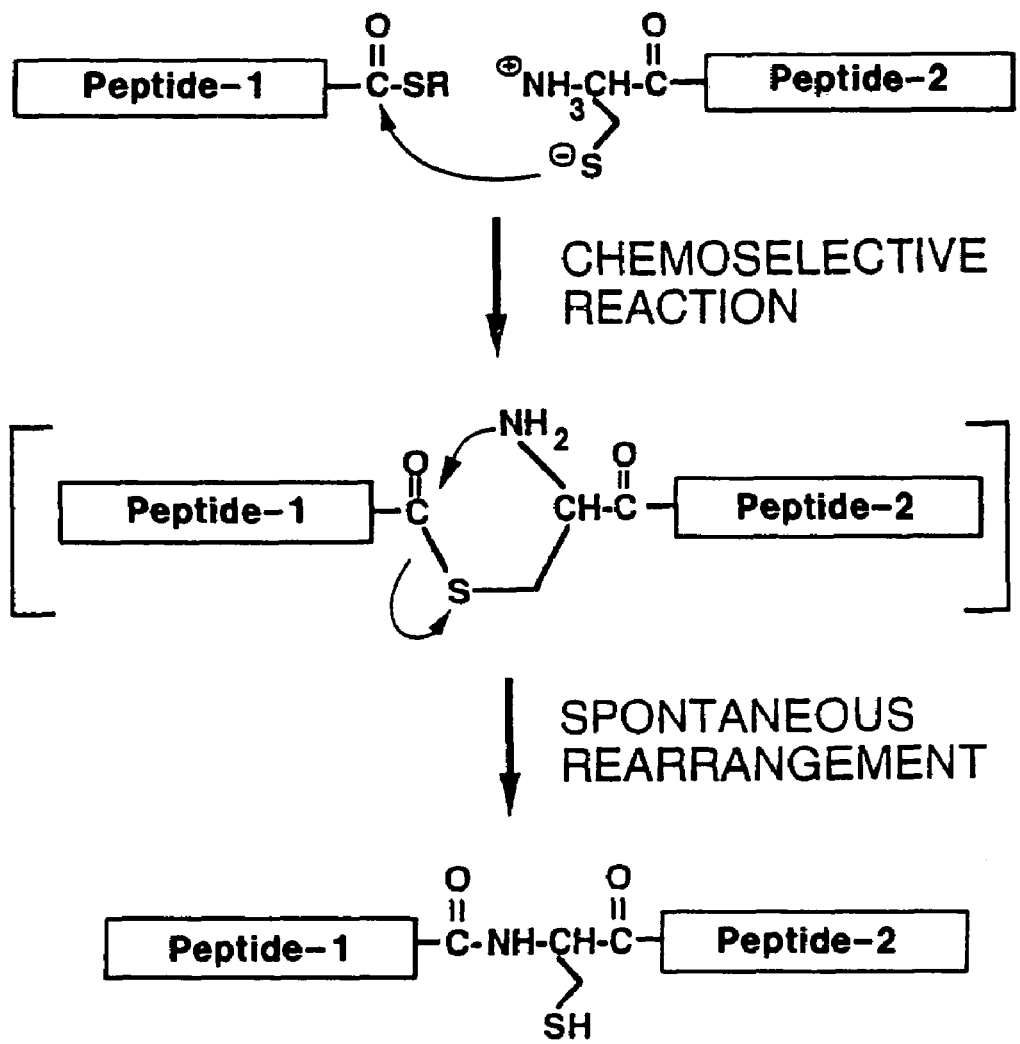
FIG. 1 illustrates the overall principle of 'native chemical ligation.'
Figure 2:
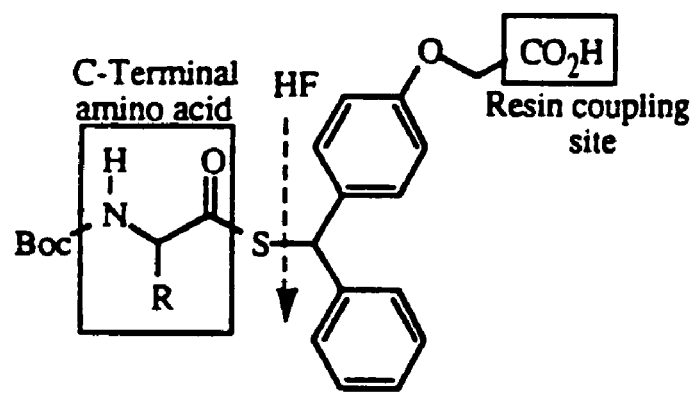
FIG. 2 illustrates a general synthesis of Boc-amino thioester linker (1), dicyclohexylamine salt.
Figure 2:
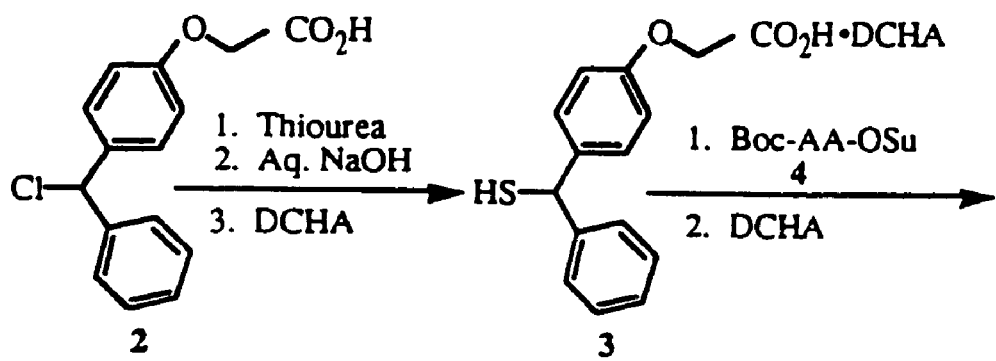
Figure 2:
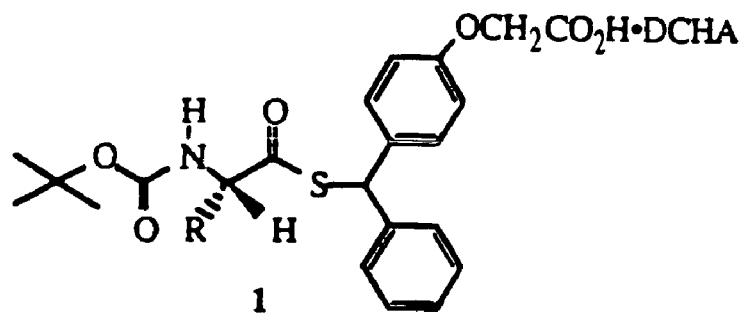
Figure 3A:
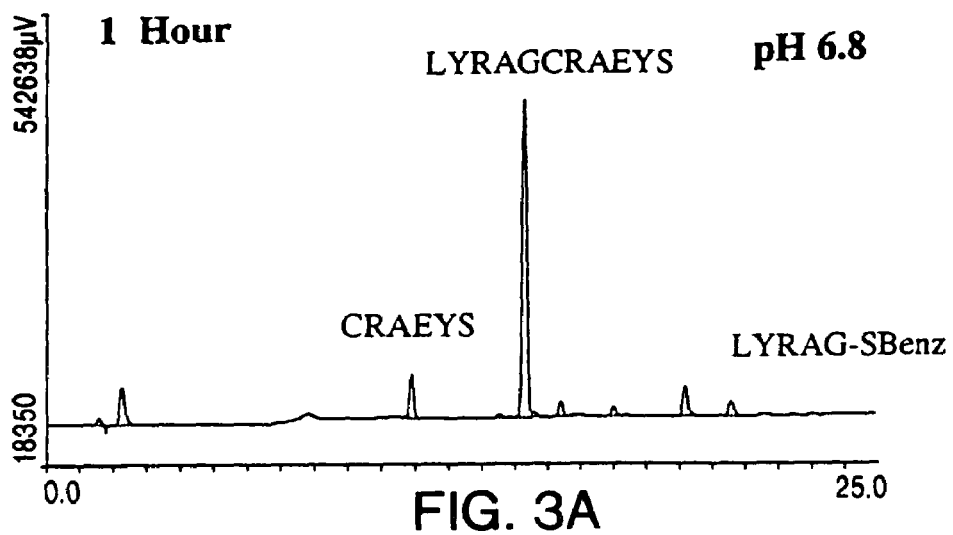
FIG. 3 illustrates the progress of a first native chemical ligation reaction for the production of model peptide (Sequence No. 5) of Example 1 using a first peptide segment (Sequence No. 2) and a second peptide seguement (Sequence No. 3) having a S-benzyl derivative, as monitored by HPLC.
Figure 3B:
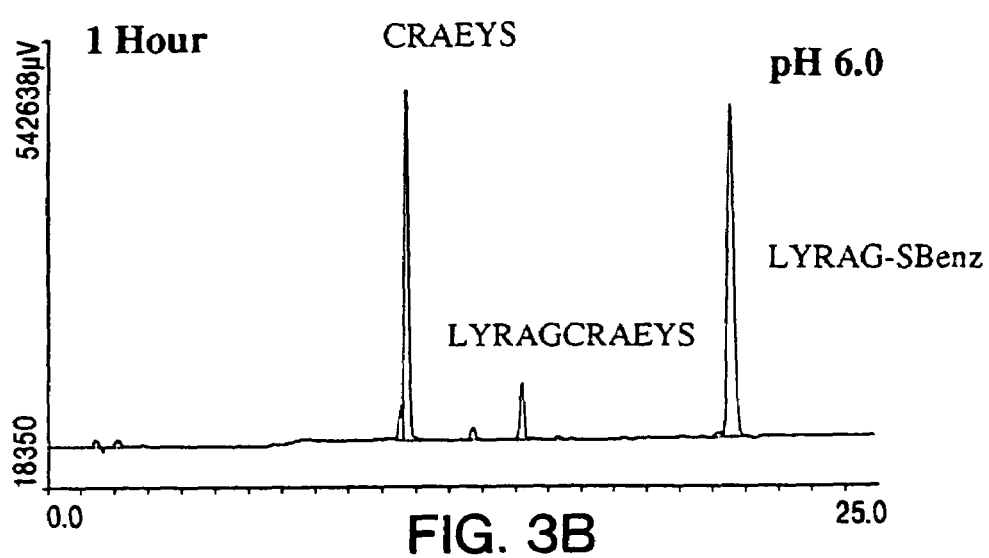
Figure 3C:
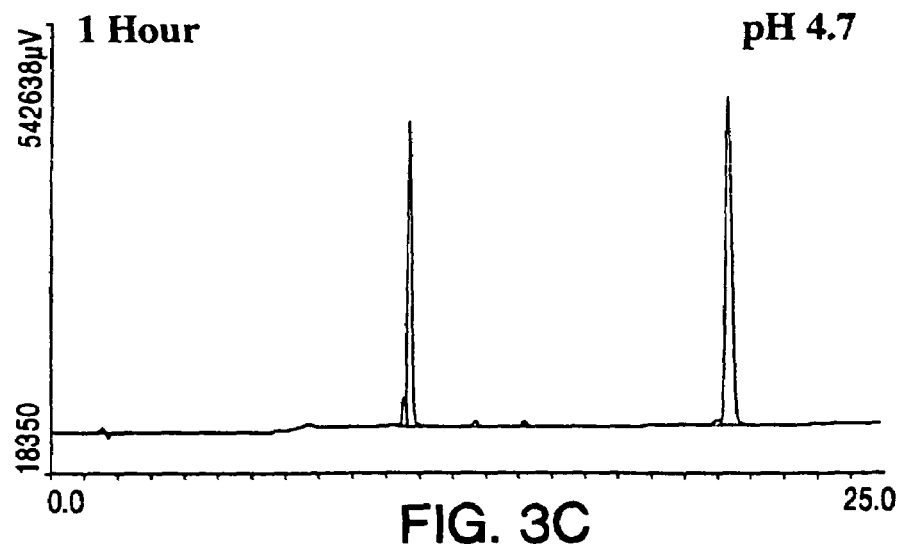

A typical procedure for the formation and utilization of the thioester resin linker for use in the solid phase synthesis of peptide-α-thioacids is as follows: (Kent et. al. *Tetrahedron Lett.* (1995): vol. 36, p 1217).

4-(α-Mercaptobenzyl)phenoxyacetic acid, dicyclo-hexylamine (3) Scheme 2. A mixture of 2, formed using the conditions as established by Yamashiro et. al. *Int. J. Pept. Protein Res.* (1988): vol. 31, pp 322-334, (7.5 grams, 27 mmol), thiourea (2.3 g, 30 mmol), and ethanol (100 mL) were heated to reflux (conditions as reported by Koenig et al *J. Org. Chem.* (1958): vol. 23, pp 1525-1530). After 4 hours, conversion to the thiouronium salt was essentially complete as shown by TLC (90:5:5 chloroform:Methanol:Acetic acid). 10N NaOH (30 ml) was added and the reflux continued for 2-3 hours. After cooling to room temperature, the reaction mixture was concentrated in vacuo to approximately half the original volume, acidified with concentrated HCl (to pH 2.0), and extracted with ethylacetate (4×30 mL). The combined ethylacetate extracts were washed with saturated NaCl (1×30 mL) and dried over $MgSO_4$. The volatile materials were removed in vacuo. The resulting oil was dissolved in ethylacetate (100 mL) and any insoluble material filtered. DCHA (dicyclohexylamine—available from Aldrich company), (6.0 mL, 30 mmol) was added to the filtrate with stirring. Within a few minutes, a white solid began to precipitate. Diethylether (150 mL) was added and the suspension cooled at −20° C. for several hours. The resulting white solid was filtered, washed with Diethylether, and dried under vacuum to give 3 (10.3 g, 23 mmol, 84%): $^1$H NMR (CDCl$_3$): δ 7.30 (m, 7H), 6.82 (d, 2H, J=8.7 Hz), 5.39 (br s, 1H), 4.40 (s, 2H), 2.81 (m, 2H), 2.23 (br s, 1H, ex D$_2$O), 1.88-1.02 (comp m, 20H); FAB MS (cesium ion): calc for [$C_{27}H_{37}NO_3S$, H$^+$] 456.2572, found 456.2572. Anal. Calcd for $C_2H_{37}NO_3S$: C, 71.17; H, 8.18; N, 3.07; S, 7.04. Found: C, 71.11; H, 8.41; N, 3.08; S, 7.09.

General Synthesis of Boc-amino thioester linker (1), dicyclohexylamine salt (scheme 2). A mixture of 3 (3.67 mmol), Boc-Ala-OSu (available from Novabiochem Corp.) (3.68 mmol), DIEA (diisopropylethylamine-5.74 mmol), dimethylformamide (35 mL) and methylene chloride (4 mL) was stirred at room temperature. After several hours, the initial white suspension completely dissolved to give a clear, colorless solution. After 24 hours, the reaction mixture was poured into 1N HCl (150 mL) and extracted with ethylacetate (4×35 mL). The combined ethylacetate extracts were washed with 1N HCl (2×30 mL), H$_2$O (1×30 mL), saturated NaCl (1×30 mL) and dried over MgSO$_4$. Volatiles were removed in vacuo. The resulting oil was purified by flash chromatography (925:50:25 Chloroform:MeOH:acetic acid) to give an oil contaminated with Acetic acid. To remove residual Acetic acid, the oil was dissolved in Chloroform (40 mL) and washed with 0.1 N HCl (7×10 mL), saturated NaCl (1×10 mL) and dried over MgSO$_4$. Volatiles were removed in vacuo to give 1 as an oil. This oil was dissolved in diethylether (10 mL) to which was added dicyclohexylamine (1 equivalents). Hexane (100 mL) was added with stirring to separate the dicyclohexylamine salt of 1 as a thick oil from any unreacted dicyclohexylamine. Solvents were decanted from the oil and the oil dissolved in CH$_2$Cl$_2$ (30-40 mL). The resulting solution was concentrated in vacuo to give the dicyclohexylamine salt 1 as a white foamy solid (scheme 2).

An example of the linkage and synthesis on the resin is as follows: 4-[α-(Boc-Ala-S)benzyl]phenoxyacetic acid (0.80 mmol) is added in 9 ml methylene chloride to 1.00 g aminomethyl-resin (0.40 mmol) and treated at 0° C. with 1.33 mL 0.6 M DCCI (dicyclohexylcarbodiimide) in methylene chloride for 15 min and at 24° C. for 30 minutes. The product is then subjected to standard solid-phase peptide synthesis conditions (Kent et. al. *Tetrahedron Letters* (1995): vol. 36, p 1217; J. Blake, *Int. J. Pept. Protein Res*. (1981): vol. 17, p 273). Once the desired chain is synthesized, the peptide resin (approx. 45 µmol original load) is treated in 8 mL liquid HF (0.8 mL anisole) at 0° C. for 1 hour. After evaporation with nitrogen, the residue is washed with ethyl acetate. The solid is subsequently stirred in water (approx. 15 mL) at 0° C. while adjusting the pH to 6.0 with solid ammonium bicarbonate. Filtration and lyophilization gives the crude thioacid product which can be further purified by preparative HPLC in 30 mg batches.

Preparation of the Thioester Terminal Peptide Segment

The A-COSR thioester peptide can be synthesized in two general ways:

(1) Reaction of a crude lyophilized thioacid peptide with Ellman's reagent (5,5'-dithiobis-2-nitrobenzoic acid, available from Aldrich company) at pH 5.5 (2.0 equivalents), 6M Guanidine in 100 mM Na acetate buffer. This gives the SNB-thioester peptide which is subsequently purified by reversed phase high performance liquid chromatography (RPHPLC).

(2) Reaction of a crude lyophilized thioacid peptide with benzyl bromide at pH 4.0, 6M guanidine and 100 mM Na acetate buffer. The benzyl thioester is then purified by RPHPLC.

The conditions stated above, permit the formation of an unprotected oligonucleotide which is equipped with the activated thioester. Subsequent reaction with a second peptide containing a terminal cysteine residue, permits a facile coupling with the formation of a native peptide bond and can generate oligopeptide chains of 100 or more amino acid residues (Scheme 1).

EXAMPLES

Example 1

The model peptide Leu-Tyr-Arg-Ala-Gly-αCOSH (Sequence No.: 1) is prepared by optimized stepwise solid-phase peptide synthesis on an aminomethyl resin. The thioester resin linker is prepared by a generalized version as adopted from Kent et. al. *Tetrahedron Letters*, (1995): vol. 36, p 1217; J. Blake, *Int. J. Pept. Protein Res*. (1981): vol. 17, p 273; D. Yamashiro and C. H. Li, ibid. (1988): vol. 31, p 322. Once the desired chain is synthesized, the peptide resin (approx. 45 μmol original load) is treated in 8 mL liquid HF (0.8 mL anisole) at 0° C. for 1 hour. After evaporation with nitrogen, the residue is washed with ethyl acetate. The solid is subsequently stirred in water (approx. 15 mL) at 0° C. while adjusting the pH to 6.0 with solid ammonium bicarbonate. Filtration and lyophilization gives the crude thioacid product which can be further purified by preparative HPLC in 30 mg batches.

The thioester terminal peptide segment is subsequently prepared from the thioacid fragment by chemical synthesis to equip it with the necessary α-COSR functionality where R is an alkyl group such as benzyl, 5-thio-2-nitrobenzoic acid (—SNB), thiophenol, etc. The use of better thioester leaving groups resulted in faster ligation reactions. Thus, the model peptide Leu-Tyr-Arg-Ala-Gly-αCOSH (Sequence No.: 1) is first converted to the thiobenzylester by reaction with benzyl bromide (15 equivalents) in 6.0 M guanidine-HCl, pH 4.6, sodium acetate buffer to form Leu-Tyr-Arg-Ala-Gly-αCOSBn (Sequence No.: 3). The resulting peptide is purified under standard reversed-phase high-performance liquid chromatography (HPLC) conditions using approximately 20-45% acetonitrile at 1% per minute; monitored at 214 nm.

For the peptide H-Cys-Arg-Ala-Glu-Tyr-Ser (Sequence No.: 2), solid phase methods allow the preparation of peptides of up to 60 residues in good yield and high purity as described in M. Schnolzer, P. Alewood, D. Alewood, S. B. H. Kent, *Int. J. Pept. Protein Res*. (1992): vol. 40, 180.

First, to explore the mechanism of the reaction, the peptide Leu-Tyr-Arg-Ala-Gly-αCOSBn (Bn, benzyl; sequence No.: 3) was reacted with Ac-Cys (containing a blocked α-$NH_2$ functional group—commercially available from Novabiochem corp.). The exact mass of the resulting ligation product, Leu-Tyr-Arg-Ala-Gly-αCOS-$CH_2$C(NHAc)$CO_2$H (Sequence No.: 4), was determined by electrospray mass spectrometry and was consistent with a thioester-linked peptide as the ligation product generated by nucleophilic attack of the Ac-Cys side chain on the α-thioester moiety of the peptide.

Finally, the reaction of Leu-Tyr-Arg-Ala-Gly-αCOSBn (Sequence No.: 3) with Cys-Arg-Ala-Glu-Tyr-Ser (Sequence No.: 2, containing an unblocked α-$NH_2$ functional group) proceeded rapidly at pH 6.8 (below pH 6.0, the reaction proceeded very slowly, suggesting the involvement of the ionized thiolate of the Cys side chain at pH 6.8; scheme 3) and gave a single product of the expected mass. The peptides Leu-Tyr-Arg-Ala-Gly-αCOSBn+Cys-Arg-Ala-Glu-Tyr-Ser were reacted in 0.1 M phosphate buffer at pH 6.8, 6.0 and 4.7 at 25° C. After 1 hour, the reactions had proceeded as follows: at pH 6.8 >95%; at pH 6.0 approximately 10%; and at pH 4.7, approximately 1.0% of ligated product Leu-Tyr-Arg-Ala-Gly-Cys-Arg-Ala-Glu-Tyr-Ser (Sequence No.: 5). As observed by HPLC, scheme 3 shows the pH dependence of the reaction after 1 hour and at 25° C. This product lacked susceptibility to nucleophiles and had the ability to form disulfide-linked dimeric peptides, indicating unambiguously the formation of a native amide bond at the ligation site.

Figure 4:
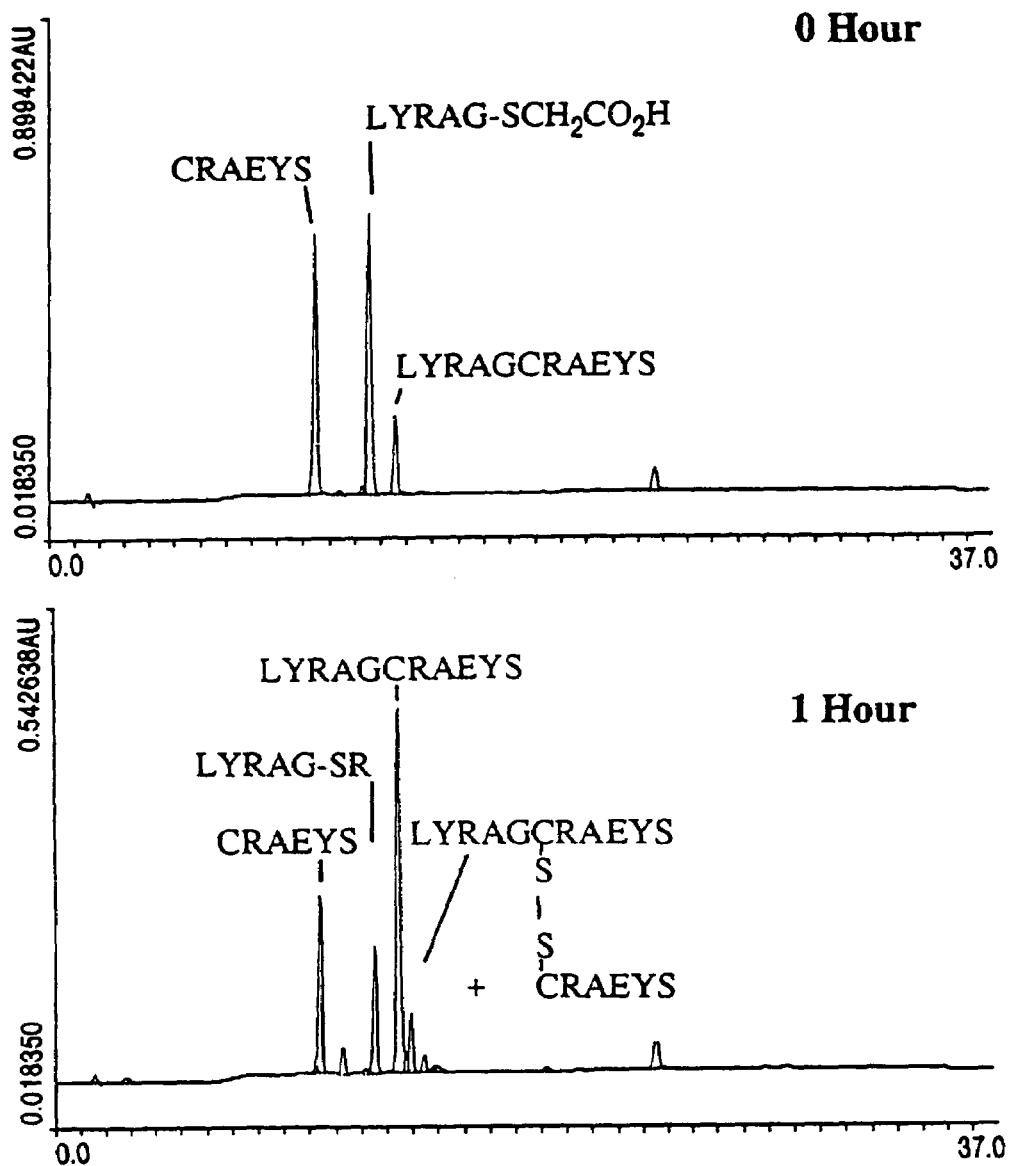
FIG. 4 illustrates the progress of a second native chemical ligation reaction for the production of model peptide (Sequence No. 5) of Example 1 using a first peptide segment (Sequence No. 2) and a second peptide seguement (Sequence No. 6) having a thioacetic acid derivative, as monitored by HPLC.
Figure 5:
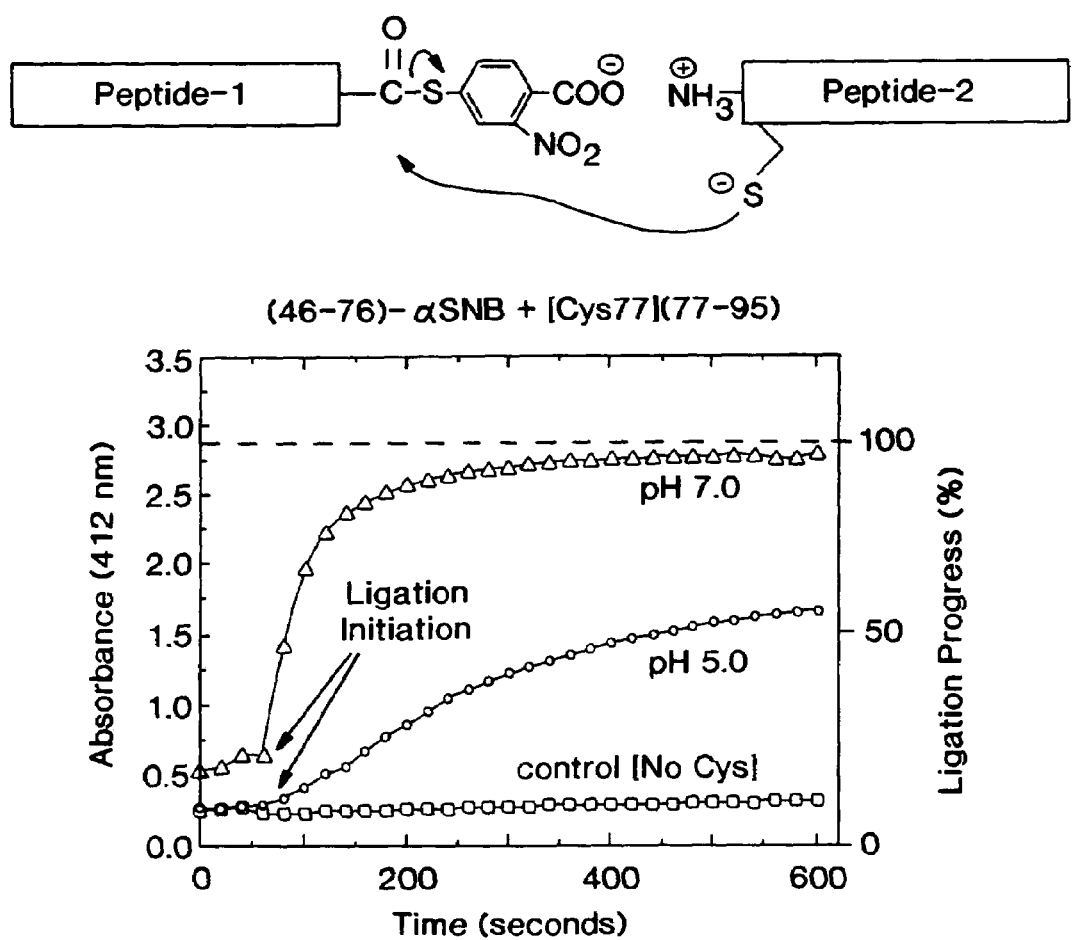
FIG. 5 illustrates the kinetics of the native chemical ligation reaction of Example 2 with respect to the linkage of peptide segments 46-76 and 77-95 for producing IL-3 receptor β-subunit.
Figure 6:
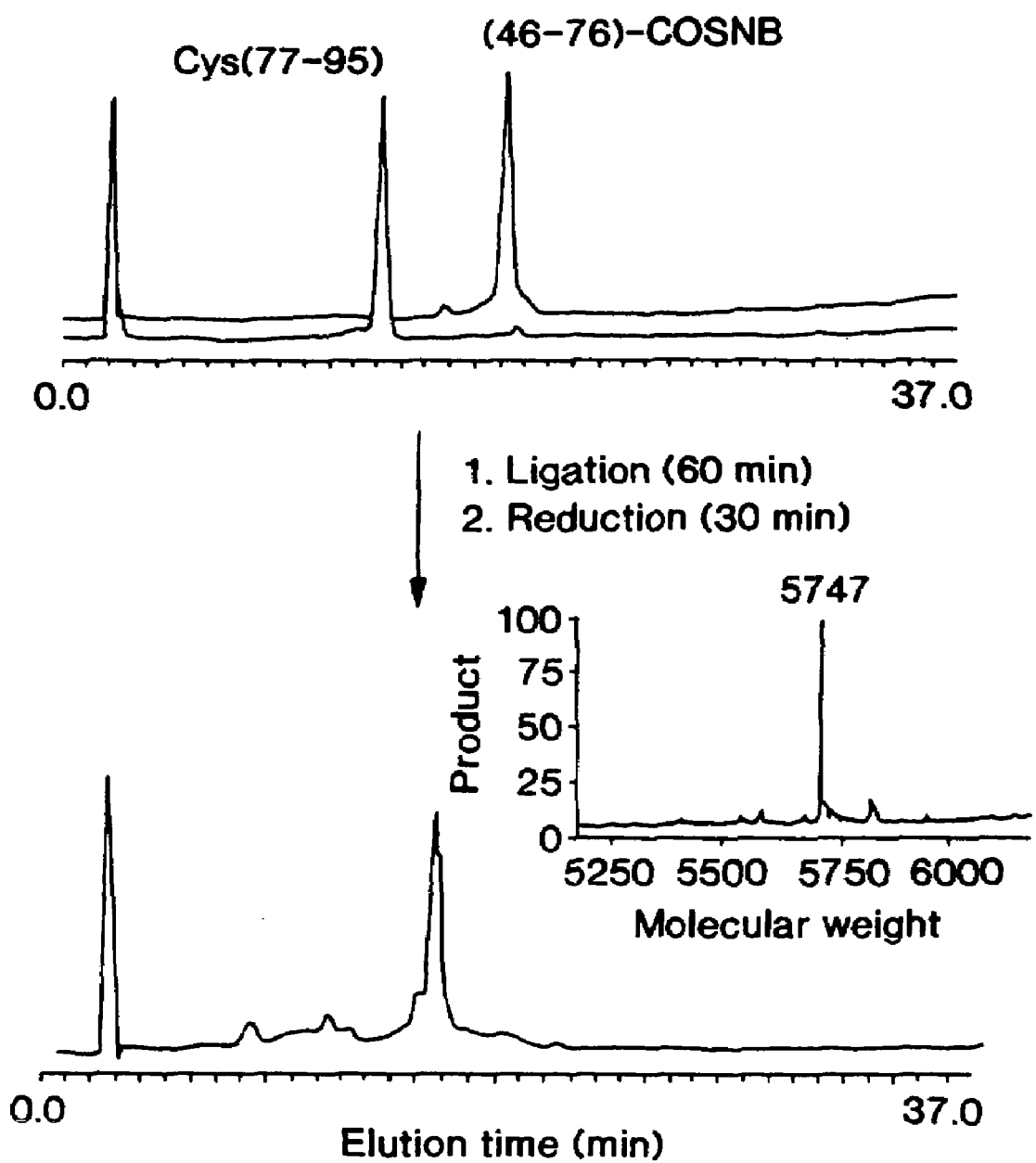
FIG. 6 illustrates the reversed-phase HPLC purification and electrospray mass spectroscopy of unreacted IL-3 peptide segments (46-76) and (77-95) of IL-3 receptor β-subunit and of their native chemical ligation product as detailed in Example 2.
Figure 7:
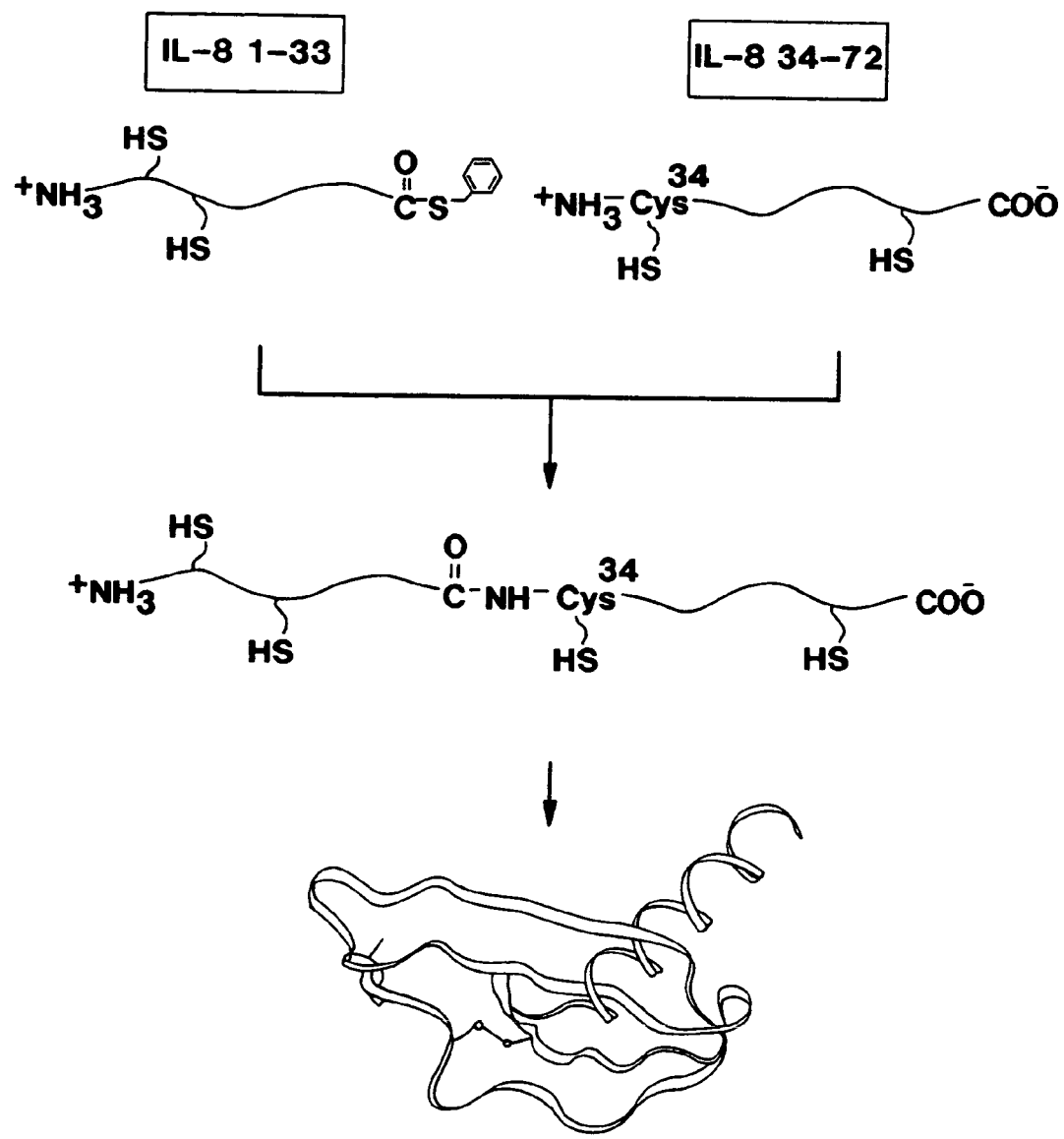
FIG. 7 illustrates a native chemical ligation scheme for producing LI-8 as detailed in Example 3.
Figure 8A:
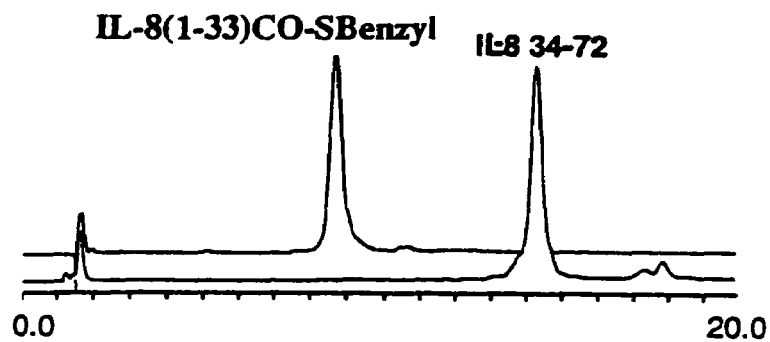
FIG. 8 illustrates the reversed-phase HPLC purification and electrospray mass spectroscopy of IL-8 (Sequence No.: 10) as formed by a native chemical ligation of peptides Sequence No.'s 8 and 9 in Example 3.
FIG. 8B illustrates the unreacted IL-8 peptides (1-33)-SBenzyl (Sequence No. 8) and IL-8 34-72 (Sequence No. 9) prior to ligation.
FIG. 8C illustrates the unfolded IL-8 ligation product, Sequence No. 10.
FIG. 8D illustrates the folded IL-8 ligation product, Sequence No. 10.
Figure 8B:
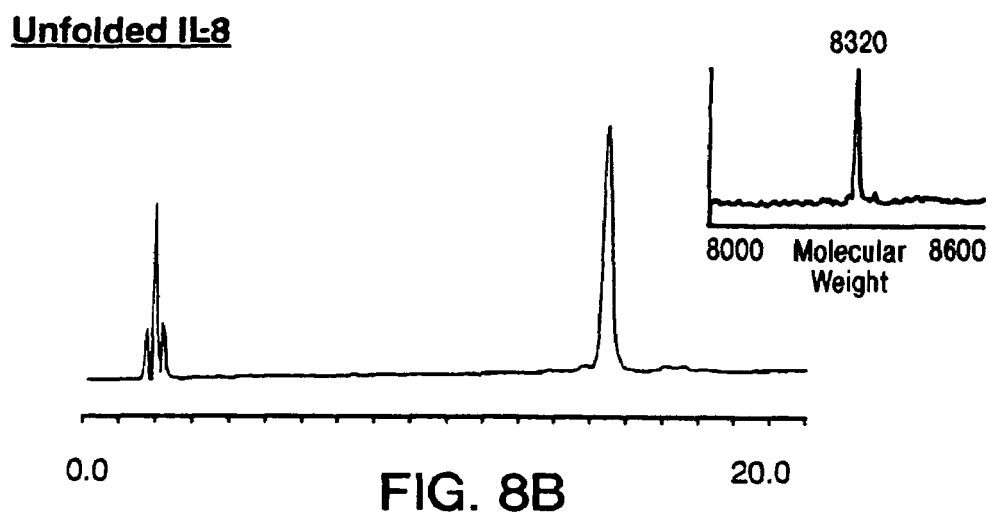
Figure 8C:
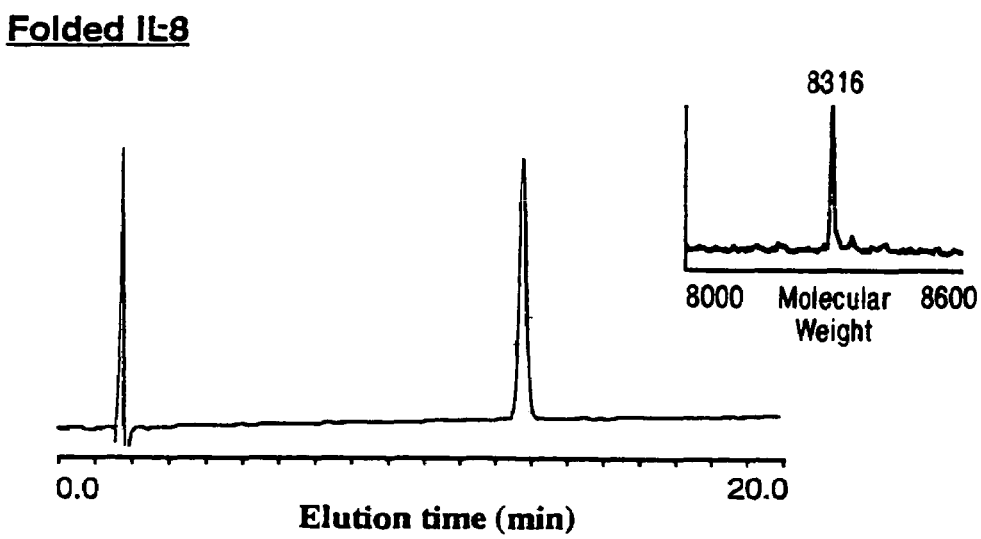
Figure 9:
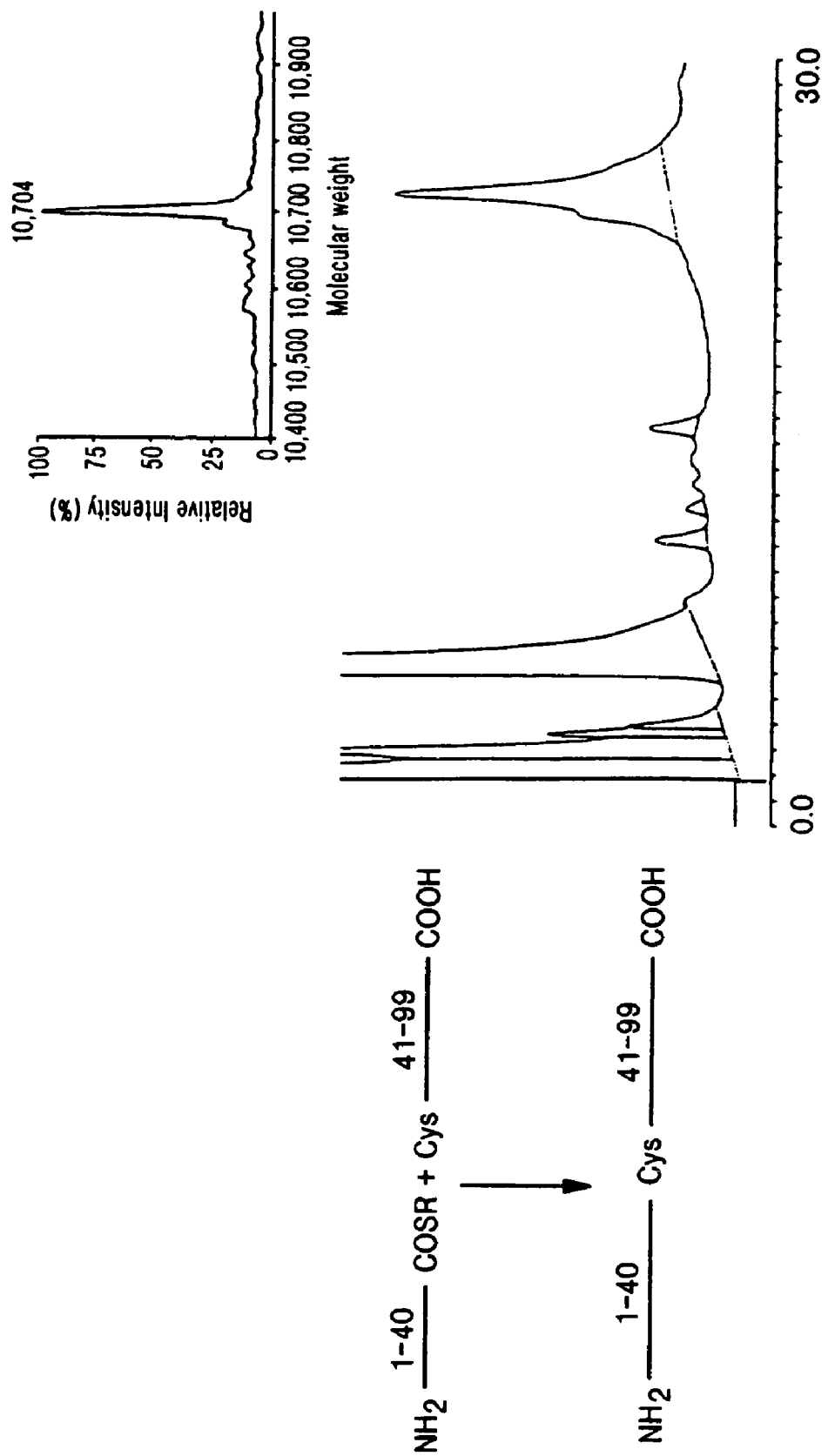
FIG. 9 illustrates the reversed-phase HPLC purification and electrospray mass spectroscopy of HIV-1 K41 protease (Sequence No.: 15) as formed by native chemical ligation of peptides Sequence No.'s 11 and 12 in Example 4.
Figure 10A:
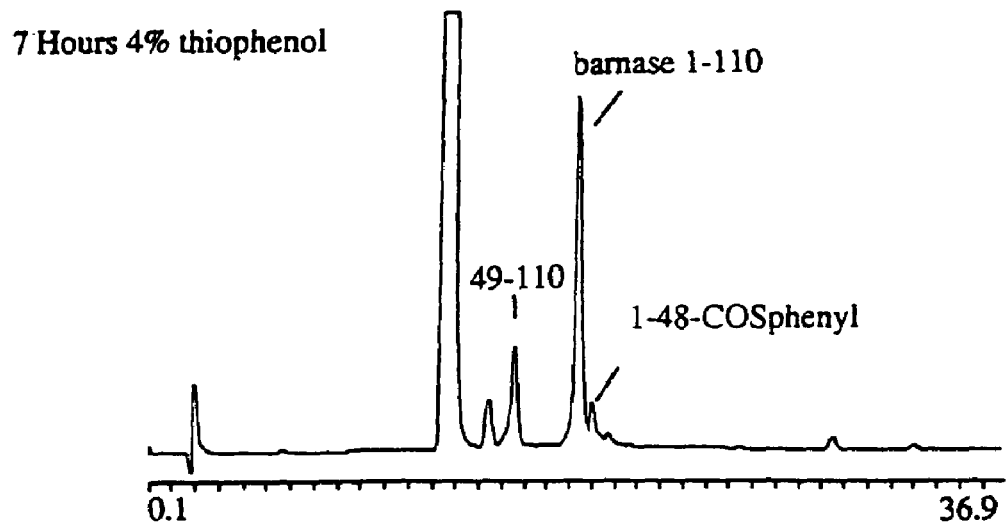
FIG. 10 illustrates the reversed-phase HPLC purification of Barnase K39 (Sequence No.: 20) as formed by native chemical ligation of peptide Sequence No's. 17 and 18 in Example 5.
Figure 10B:
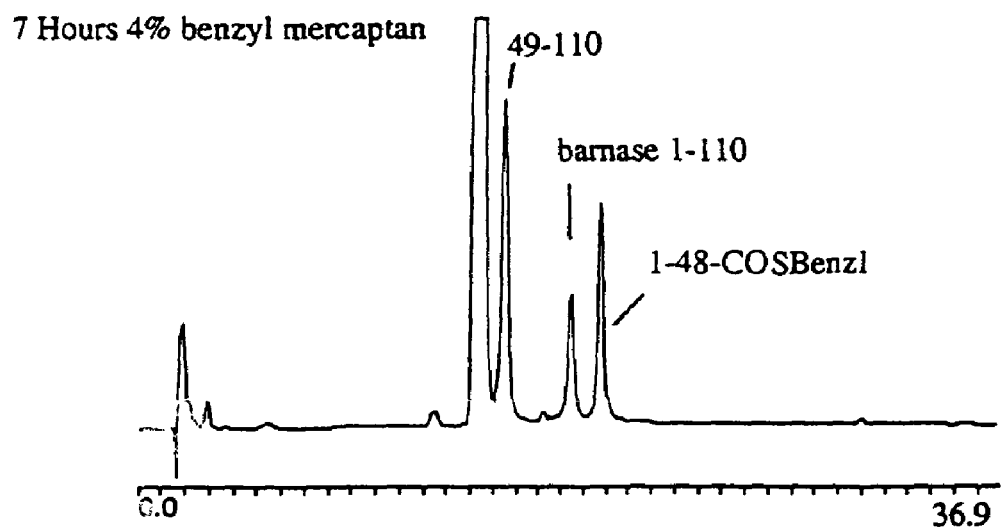

Another, unpublished model using the 2-thioacetic acid derivative Leu-Tyr-Arg-Ala-Gly-SCH$_2$COOH (SEQ ID NO 6), formed from attack of the thioacid Leu-Tyr-Arg-Ala-Gly-SH (SEQ ID NO 1), onto 2-bromoacetic acid in methylene chloride)+Cys-Arg-Ala-Glu-Tyr-Ser (Sequence No.: 2) was ligated at pH 6.8 in 0.2 M phosphate buffer, at 45° C. After 1.0 hour the reaction had proceeded to 80% as observed in FIG. 4 by HPLC. The isolation of oxidation products from the ligated Leu-Tyr-Arg-Ala-Gly-Cys-Arg-Ala-Glu-Tyr-Ser (SEQ ID NO 5) and unreacted Cys-Arg-Ala-Glu-Tyr-Ser (SEQ ID NO 2) demonstrated the presence of a free thiol ligation product.

The native chemical ligation procedure is generally applicable to peptides containing the full range of functional groups, normally found in proteins. Even free internal Cys residues may be present in either of the reacting segments. Internal Cys residues can undergo ester exchange with the peptide-α-thioester component; however, this reaction is unproductive because no rearrangement to the amide bond can occur, the thioester formed is readily reversible and remains a productive part of the reacting system.

The native chemical ligation procedure is limited to reaction at an amino-terminal Cys residue. To prevent the side chain thiol of this Cys from oxidizing to form a disulfide-linked dimer, an excess of thiol corresponding to the thioester leaving group is used to keep the Cys residues in reduced form without interfering with the ligation reaction. In addition, small amounts of low molecular weight thiols such as benzyl mercaptan or thiophenol are added to the coupling reaction mixture to maintain a reducing environment.

The addition of thiols increases the reactivity of the thioester, particularly if the added thiol is a better leaving group than the pre-formed thioester. An example of this observation is when the benzyl ester is converted to a phenyl ester by addition of thiophenol to reaction. Reaction yields and rates are substantially increased. For example, after 7 hours with benzyl mercaptan, the Barnase reaction yielded 25%, while the thiophenol treatment to the same reaction mixture yielded 90%).

Addition of thiols to the ligation mixture also keeps the reaction mixture in a reduced form. This prevents oxidation of the reactive N-terminal Cys residues and when internal Cys residues are present, the thiols reduce the formation of intramolecular disulfide bonds. Additionally, the reducing environment increases the stability of the thioester segment (ligation reactions can proceed overnight with little or no hydrolysis at pH 7.5).

Example 2

A rapid native chemical ligation is illustrated by the synthesis of a peptide segment corresponding to residues 46 to 95 from the external domain of the human IL-3 receptor β-subunit incorporated herein: R. D'Andrea et. al., *Blood* (1994): vol. 83, p 2802.

Crude synthetic IL-3 Msc(46-76)αCOSH was converted to the 5 thio-2-nitrobenzoic acid ester (—COSNB) by treatment with 5,5'-dithio-bis(2-nitrobenzoic acid) [10 equivalents (eq)] in 8 M urea, pH 4.0, 50 mM ammonium acetate buffer [Msc, 2 (methyl-sulfonyl)-ethyloxy-carbonyl (Fluka #69227) protecting group is placed on the N-terminus using 1.1 equivalents (eq.) 2-(methylsulfonyl)ethyl 4-nitrophenyl carbonate, 1.1 eq. diisopropylethylamine, and 0.5 M dimethylformamide). This thioester-containing material was found to be completely stable below pH 6.0, and was readily purified under standard reversed-phase HPLC conditions using approximately 20-45% acetonitrile at 1% per minute and monitored at 214 nm.

As shown in scheme 5, ligation is initiated by adding IL-3 [Cys77](77-95) (prepared by standard solid phase methods Kent et al., *Int. J. Pept. Protein Res.* (1992): vol. 40, 180) to purified IL-3 Msc(46-76)αCOSNB at the stated pH and the reaction is monitored by UV [the substituted aryl thiolate leaving group has a characteristic UV absorption at 412 nm ($\epsilon_{TNB, 412\,nm} = 13,700\,dm^3\,mol^{-1}\,cm^{-1}$)]. At pH 7.0, the reaction is essentially complete within 5 min. No reaction is observed when Msc(46-76)αCOSNB is exposed to a 10-fold molar excess of Leu-enkephalin (amino-terminal residue, Tyr) at pH 5.0. This control experiment confirms the absolute requirement for an amino-terminal Cys residue at the site of ligation (scheme 5).

Purified IL-3 [Cys77](77-95) (0.98 mM) and IL-3 (46-76) αCOSNB (0.9 mM) were reacted in 8 M urea, pH 5.0, 50 mM ammonium acetate buffer at 23° C. (monitored by analytical HPLC 9C18 reversed phase 22.5 to 45% acetonitrile at 0.7% per minute; 214 nm). After 1 hour, the ligation solution is exposed to the reducing agent tris(2-carboxyethyl)phosphine (TCEP) at pH 9.0 and subsequently raised to pH 13.0 to remove the Msc protecting group (Treatment with TCEP was found to aid in the purification and analysis of product by reducing the thiophenol and benzyl mercaptan disulfide products which had a tendency to co-elute with the peptide products). Scheme 6 shows the progress of the reaction by HPLC; conversion of the starting peptides to the crude product is shown (scheme 6). The 50 residue product has the expected molecular mass by electrospray mass spectrometry [observed, 5747.0 daltons; calculated (average isotope composition), 5747.4 daltons]. The ligation product is shown to be stable at high pH, reducing conditions, and forms an intramolecular disulfide bond. These observations are consistent with the presence of a native peptide bond at the site of ligation.

Analogous methods have required removal of protecting groups (J. Blake et. al., *Int. J. Pept. Protein Res.* (1981): vol. 17, p 273; Kemp et. al. *J. Org. Chem.* (1993): vol. 58, p 2216; Liu et. al. *J. Am. Chem. Soc.* (1994): vol. 116, 4149) or conversion of intermediates to the final form, or both steps. No previous method has allowed the chemical reaction of unprotected peptide segments to directly yield a native backbone final product.

Example 3

The IL-8(34-72) segment (Sequence No. 9) is prepared by optimized stepwise solid-phase methods as described by Kent et al., *Int. J. Pept. Protein Res.* (1992): vol. 40, 180 and yield peptides from 60-80 residues in good yields and high purities. The peptide-αCOSH is prepared by optimized stepwise solid-phase peptide synthesis on a aminomethyl resin with a thioester linker. The thioester linker is prepared by a generalized version as adopted from J. Blake, *Int. J. Pept. Protein Res.* (1981): vol. 17, p 273; D. Yamashiro and C. H. Li, ibid. vol. 31, 322 (1988). Products are subsequently purified by standard reversed-phase HPLC conditions and characterized by standard methods which include electrospray mass spectrometry.

Crude synthetic segment IL-8(1-33)αCOSH (Sequence No.: 7) is converted to the thiobenzyl ester by reaction with benzyl bromide (15 equivalents) in 6 M guanidine-HCl at pH 4.6 in 100 mM sodium acetate buffer. The reaction mixture is purified under standard reversed-phase HPLC conditions and forms the thiobenzyl ester, IL-8(1-33)αCOSBn (Sequence No.: 8), (Scheme 7).

The segments IL-8(1-33)αCOSBn (Sequence No.: 8), (5.0 mg, 1.3 µmol) and IL-8(34-72) (Sequence No. 9), (4.8 mg, 1.1 mmol) were reacted in 0.5 ml 6.0 M guanidine-HCl, pH 7.6, phosphate buffer at 23° C. in the presence of benzyl mercaptan (5 ml). After suitable reaction time (48 to 72 hours), a ligation yield of approximately 60% was obtained. The product was purified by standard reversed-phase HPLC as described via supra and characterized by electrospray mass spectroscopy.

As shown in scheme 8B, an analytical HPLC spectrum ($C_{1-8}$ reversed phase; 25 to 45% acetonitrile at 1% per minute; monitored at 214 nm) is shown before the reaction of the synthetic peptide segments IL-8(1-33)αCOSBzl and IL-8 (34-72).

As shown in scheme 8C, an analytical HPLC spectrum ($C_{18}$ reversed phase; 25 to 45% acetonitrile at 1% per minute; monitored at 214 nm) of the purified ligation product, IL-8 (1-72)(SH)$_4$ (Sequence No.: 10), in fully reduced form. (Inset) Electrospray mass spectrum (raw data displayed as a single charge state): observed molecular mass 8319.8 daltons; calculated molecular mass (average isotope composition), 8319.8 daltons.

As shown in scheme 8D, air oxidation of the purified 1-72 ligation product forms the folded [Ala$^{33}$]IL-8 molecule, shown after HPLC purification. The earlier elution of the folded, disulfide cross-linked native protein compared with the reduced polypeptide is typical (see Lewis et. al *FEB Lett.* (1989): vol. 307, p 97; Lewis et al *J. Biol. Chem.*: vol. 269, p 16075; Lewis et. al *Biochemistry* (1991): vol. 30, 3128).

Folding and oxidation conditions: polypeptide at 0.2 mg/ml, 1M guanidine-HCl, pH 8.5 tris buffer, and vigorous stirring in air at ambient temperature (inset). Electrospray mass spectrometry of the oxidized and folded synthetic IL-8 (raw data displayed as a single charge state). Observed molecular mass, 8315.6 daltons; calculated molecular mass (average isotope composition), 8315.8 daltons. (Scheme 8).

Example 4

HIV-1 K41 Protease

Unpublished Conditions

Ligation reactions are performed in several ways. An optimized procedure for a ligation reaction involving a (5-thio-2-nitrobenzoic acid) SNB thioester is to weigh the two peptides, HIV (1-40)-COSNB (Sequence No.: 11, formed from standard conditions stated herein) and HIV (41-99) (Sequence No.: 12, formed from standard conditions stated herein), as solids in the same reaction vessel and add 6.0 M guanidine HCl pH 6.5 with 100 mM Na acetate (the approximate peptide concentration is 7-13 mg/mL of each peptide).

After 5 min, approx. 2.0% thiol is added. Two thiol catalysts have been used, viz. benzyl mercaptan (forms the benzyl thioester in situ; Sequence No.: 13) and thiophenol (forms the phenyl thioester in situ; Sequence No.: 14). In the ligation of HIV PR, reaction with benzyl mercaptan gave greater than 60% product yield in 40 hours while the thiophenol gave greater than 80% product yield in 10 hours to form HIV-1 K41 protease (Sequence No.: 15).

Subsequent treatment with TCEP was found to aid in the purification and analysis of product by reducing the thiophenol and benzyl mercaptan disulfide products which tend to co-elute with peptide products. The product was purified by standard reversed-phase HPLC as described via supra and characterized by electrospray mass spectroscopy (Scheme 9).

Example 5

Barnase Example

Unpublished Conditions

The two peptides Barnase (1-48)-SNB (Sequence No.: 16, formed from standard conditions stated herein) and Barnase (49-110), (Sequence No.: 17, formed from standard conditions stated herein) were weighed as solids in the same reaction vessel and dissolved in pH 7.5 buffer (6M Guanidine 100 mM phosphate). Immediately upon dissolving the peptides, 2% benzyl mercaptan (forms the benzyl thioester in situ; Sequence No.: 18) or 4% thiophenol (forms the phenyl thioester in situ; Sequence No.: 19) was added. After 7 hours, the benzyl mercaptan reaction proceeded 25% and the thiophenol reaction proceeded to >90% to form Barnase (1-110) (Sequence No.: 20). The product was purified by standard reversed-phase HPLC as described via supra (scheme 10).

The addition of thiols increases the reactivity of the thioester, particularly if the added thiol is a better leaving group than the pre-formed thioester. An example of this observation is when the benzyl ester is converted to a phenyl ester by addition of thiophenol to reaction. Reaction yields and rates are substantially increased. For example, after 7 hours with benzyl mercaptan, the Barnase reaction yielded 25%, while the thiophenol treatment to the same reaction mixture yielded 90% to form Barnase (1-110) (Sequence No.: 20).

Addition of thiols to the ligation mixture also keeps the reaction mixture in a reduced form. This prevents oxidation of the reactive N-terminal Cys residues and when internal Cys residues are present, the thiols reduce the formation of intramolecular disulfide bonds. Additionally, the reducing environment increases the stability of the thioester segment (ligation reactions can proceed overnight with little or no hydrolysis at pH 7.5).

What is claimed is:

1. A method for producing a desired protein or domain thereof, which comprises admixing:
   (I) a first oligopeptide, said first oligopeptide comprising a fragment of said desired protein or domain thereof, and having a C-terminal thioester; and
   (II) a second oligopeptide, said second oligopeptide comprising a fragment of said desired protein or domain thereof, and having an N-terminal cysteine amino acid residue having an unoxidized sulfhydryl side chain and a free amino group that is capable of forming a β-aminothioester linkage with said C-terminal thioester that rearranges to form an amide bond therein between;
   wherein said admixing is conducted under conditions sufficient to permit the formation of an amide bond between the C-terminus of said first oligopeptide and the N-terminus of said second oligopeptide.

2. The method of claim 1, wherein said desired protein is a naturally isolatable protein.

3. The method of claim 1, wherein said desired protein is a derivative of a naturally isolatable protein that contains one or more variant residues that are not found in said naturally isolatable protein.

4. The method of any of claim 2 or 3, wherein said protein is a mammalian protein.

5. The method of claim 4, wherein said mammalian protein is a human protein.

6. The method of claim 5, wherein said human protein is a cytokine.

7. A synthetically produced protein intermediate having greater than about 35 amino acid residues, said protein being produced by a process of ligating together a first oligopeptide fragment and a second oligopeptide fragment:

said first oligopeptide fragment having a length of 30 or more amino acid residues said synthetically produced protein intermediate being represented by the following structure:

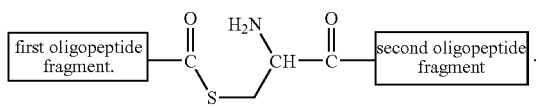

8. The synthetically produced protein intermediate of claim 7, wherein said protein intermediate has greater than about 70 amino acid residues.

9. The synthetically produced protein intermediate of claim 8, wherein said synthetically produced protein intermediate being intermediate to a mammalian protein.

10. The synthetically produced protein intermediate of claim 9, wherein said mammalian protein is a human protein.

11. The synthetically produced protein intermediate of claim 10, wherein said human protein is a cytokine.

12. A method for producing a desired protein or domain thereof, which comprises admixing:

(I) a first oligopeptide, said first oligopeptide comprising a fragment of said desired protein or domain thereof, and having a C-terminal thioester; and (II) a second oligopeptide, said second oligopeptide comprising a fragment of said desired protein or domain thereof, and having an N-terminal cysteine amino acid residue having an unoxidized sulfhydryl side chain and a free amino group that is capable of forming a β-aminothioester linkage with said C-terminal thioester that rearranges to form an amide bond therein between;

wherein said admixing is conducted under conditions sufficient to permit the formation of an amide bond between the C-terminus of said first oligopeptide and the N-terminus of said second oligopeptide;

wherein said desired protein is a derivative of a naturally isolatable protein, said desired protein containing one or more cysteine residues that are not found in said naturally isolatable protein.

* * * * *

SEQUENCE LISTING

```
<160> NUMBER OF SEQ ID NOS: 20

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence:  peptide
<221> NAME/KEY: SITE
<222> LOCATION: (5)
<223> OTHER INFORMATION: wherein COSH is thioacid

<400> SEQUENCE: 1

Leu Tyr Arg Ala Gly
  1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence:  peptide

<400> SEQUENCE: 2

Cys Arg Ala Glu Tyr Ser
  1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence:  peptide
<221> NAME/KEY: SITE
<222> LOCATION: (5)
<223> OTHER INFORMATION: wherein COSBn is benzyl thioester

<400> SEQUENCE: 3
```

```
Leu Tyr Arg Ala Gly
 1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: peptide
<221> NAME/KEY: SITE
<222> LOCATION: (5)
<223> OTHER INFORMATION: wherein Gly is modified and represented by Gly-
      alphaCOS-CH2C(NHAc)CO2H

<400> SEQUENCE: 4

Leu Tyr Arg Ala Gly
 1               5

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: peptide

<400> SEQUENCE: 5

Leu Tyr Arg Ala Gly Cys Arg Ala Glu Tyr Ser
 1               5                  10

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: peptide
<221> NAME/KEY: SITE
<222> LOCATION: (5)
<223> OTHER INFORMATION: wherein SCH2COOH is 2-thioacetic acid

<400> SEQUENCE: 6

Leu Tyr Arg Ala Gly
 1               5

<210> SEQ ID NO 7
<211> LENGTH: 33
<212> TYPE: PRT
<213> ORGANISM: Homo sapiens
<220> FEATURE:
<221> NAME/KEY: SITE
<222> LOCATION: (33)
<223> OTHER INFORMATION: wherein COSH is thioacid
<221> NAME/KEY: SITE
<222> LOCATION: (1)
<223> OTHER INFORMATION: wherein Msc is 2-methyl-sulfonyl-ethyloxy-
      carbonyl

<400> SEQUENCE: 7

Ser Ala Lys Glu Leu Arg Cys Gln Cys Ile Lys Thr Tyr Ser Lys Pro
 1               5                  10                  15

Phe His Pro Lys Phe Ile Lys Glu Leu Arg Val Ile Glu Ser Gly Pro
             20                  25                  30

Ala

<210> SEQ ID NO 8
<211> LENGTH: 33
<212> TYPE: PRT
<213> ORGANISM: Homo sapiens
<220> FEATURE:
```

```
<221> NAME/KEY: SITE
<222> LOCATION: (33)
<223> OTHER INFORMATION: wherein COSBn is benzyl thioester

<400> SEQUENCE: 8

Ser Ala Lys Glu Leu Arg Cys Gln Cys Ile Thr Tyr Ser Lys Pro
 1               5                  10                  15

Phe His Pro Lys Phe Ile Lys Glu Leu Arg Val Ile Glu Ser Gly Pro
                20                  25                  30

Ala

<210> SEQ ID NO 9
<211> LENGTH: 39
<212> TYPE: PRT
<213> ORGANISM: Homo sapiens

<400> SEQUENCE: 9

Cys Ala Asn Thr Glu Ile Ile Val Lys Leu Ser Asp Gly Arg Glu Leu
 1               5                  10                  15

Cys Leu Asp Pro Lys Glu Asn Trp Val Gln Arg Val Val Glu Lys Phe
                20                  25                  30

Leu Lys Arg Ala Glu Asn Ser
            35

<210> SEQ ID NO 10
<211> LENGTH: 72
<212> TYPE: PRT
<213> ORGANISM: Homo sapiens
<220> FEATURE:
<221> NAME/KEY: SITE
<222> LOCATION: (72)
<223> OTHER INFORMATION: SH4

<400> SEQUENCE: 10

Ser Ala Lys Glu Leu Arg Cys Gln Cys Ile Thr Tyr Ser Lys Pro
 1               5                  10                  15

Phe His Pro Lys Phe Ile Lys Glu Leu Arg Val Ile Glu Ser Gly Pro
                20                  25                  30

Ala Cys Ala Asn Thr Glu Ile Ile Val Lys Leu Ser Asp Gly Arg Glu
        35                  40                  45

Leu Cys Leu Asp Pro Lys Glu Asn Trp Val Gln Arg Val Val Glu Lys
    50                  55                  60

Phe Leu Lys Arg Ala Glu Asn Ser
 65                  70

<210> SEQ ID NO 11
<211> LENGTH: 40
<212> TYPE: PRT
<213> ORGANISM: Human immunodeficiency virus
<220> FEATURE:
<221> NAME/KEY: SITE
<222> LOCATION: (40)
<223> OTHER INFORMATION: wherein COSNB is 5-thio-2-nitro-benzoic acid
      ester

<400> SEQUENCE: 11

Pro Gln Ile Thr Leu Trp Lys Arg Pro Leu Val Thr Ile Arg Ile Gly
 1               5                  10                  15

Gly Gln Leu Lys Glu Ala Leu Leu Asp Thr Gly Ala Asp Asp Thr Val
                20                  25                  30

Ile Glu Glu Met Asn Leu Pro Gly
            35                  40
```

<210> SEQ ID NO 12
<211> LENGTH: 59
<212> TYPE: PRT
<213> ORGANISM: Human immunodeficiency virus
<220> FEATURE:
<221> NAME/KEY: SITE
<222> LOCATION: (27)
<223> OTHER INFORMATION: wherein Xaa is 2-Aminobutyric acid
<221> NAME/KEY: SITE
<222> LOCATION: (55)
<223> OTHER INFORMATION: wherein Xaa is 2-Aminobutyric acid

<400> SEQUENCE: 12

Cys Trp Lys Pro Lys Met Ile Gly Gly Ile Gly Gly Phe Ile Lys Val
 1               5                  10                  15

Arg Gln Tyr Asp Gln Ile Pro Val Glu Ile Xaa Gly His Lys Ala Ile
            20                  25                  30

Gly Thr Val Leu Val Gly Pro Thr Pro Val Asn Ile Ile Gly Arg Asn
        35                  40                  45

Leu Leu Thr Gln Ile Gly Xaa Thr Leu Asn Phe
    50                  55

<210> SEQ ID NO 13
<211> LENGTH: 40
<212> TYPE: PRT
<213> ORGANISM: Human immunodeficiency virus
<220> FEATURE:
<221> NAME/KEY: SITE
<222> LOCATION: (40)
<223> OTHER INFORMATION: wherein COSBn is ??
<221> NAME/KEY: SITE
<222> LOCATION: (40)
<223> OTHER INFORMATION: wherein COSBn is benzyl thio ester

<400> SEQUENCE: 13

Pro Gln Ile Thr Leu Trp Lys Arg Pro Leu Val Thr Ile Arg Ile Gly
 1               5                  10                  15

Gly Gln Leu Lys Glu Ala Leu Leu Asp Thr Gly Ala Asp Asp Thr Val
            20                  25                  30

Ile Glu Glu Met Asn Leu Pro Gly
        35                  40

<210> SEQ ID NO 14
<211> LENGTH: 40
<212> TYPE: PRT
<213> ORGANISM: Human immunodeficiency virus
<220> FEATURE:
<221> NAME/KEY: SITE
<222> LOCATION: (40)
<223> OTHER INFORMATION: wherein COSPh is phenyl thioester

<400> SEQUENCE: 14

Pro Gln Ile Thr Leu Trp Lys Arg Pro Leu Val Thr Ile Arg Ile Gly
 1               5                  10                  15

Gly Gln Leu Lys Glu Ala Leu Leu Asp Thr Gly Ala Asp Asp Thr Val
            20                  25                  30

Ile Glu Glu Met Asn Leu Pro Gly
        35                  40

<210> SEQ ID NO 15
<211> LENGTH: 99
<212> TYPE: PRT
<213> ORGANISM: Human immunodeficiency virus
<220> FEATURE:

```
<221> NAME/KEY: SITE
<222> LOCATION: (67)
<223> OTHER INFORMATION: wherein Xaa is amino butyric acid
<221> NAME/KEY: SITE
<222> LOCATION: (95)
<223> OTHER INFORMATION: wherein Xaa is 2-Aminobutyric acid

<400> SEQUENCE: 15
```

Pro Gln Ile Thr Leu Trp Lys Arg Pro Leu Val Thr Ile Arg Ile Gly
1               5                   10                  15

Gly Gln Leu Lys Glu Ala Leu Leu Asp Thr Gly Ala Asp Asp Thr Val
            20                  25                  30

Ile Glu Glu Met Asn Leu Pro Gly Cys Trp Lys Pro Lys Met Ile Gly
        35                  40                  45

Gly Ile Gly Gly Phe Ile Lys Val Arg Gln Tyr Asp Gln Ile Pro Val
    50                  55                  60

Glu Ile Xaa Gly His Lys Ala Ile Gly Thr Val Leu Val Gly Pro Thr
65                  70                  75                  80

Pro Val Asn Ile Ile Gly Arg Asn Leu Leu Thr Gln Ile Gly Xaa Thr
                85                  90                  95

Leu Asn Phe

```
<210> SEQ ID NO 16
<211> LENGTH: 48
<212> TYPE: PRT
<213> ORGANISM: Bacillus amyloliquefaciens
<220> FEATURE:
<221> NAME/KEY: SITE
<222> LOCATION: (48)
<223> OTHER INFORMATION: wherein COSNB is 5-thio-2-nitro benzoic acid
      ester

<400> SEQUENCE: 16
```

Ala Gln Val Ile Asn Thr Phe Asp Gly Val Ala Asp Tyr Leu Gln Thr
1               5                   10                  15

Tyr His Lys Leu Pro Asn Asp Tyr Ile Thr Lys Ser Glu Ala Gln Ala
            20                  25                  30

Leu Gly Trp Val Ala Ser Lys Gly Asn Leu Ala Asp Val Ala Pro Gly
        35                  40                  45

```
<210> SEQ ID NO 17
<211> LENGTH: 62
<212> TYPE: PRT
<213> ORGANISM: Bacillus amyloliquefaciens

<400> SEQUENCE: 17
```

Cys Ser Ile Gly Gly Asp Ile Phe Ser Asn Arg Glu Gly Lys Leu Pro
1               5                   10                  15

Gly Lys Ser Gly Arg Thr Trp Arg Glu Ala Asp Ile Asn Tyr Thr Ser
            20                  25                  30

Gly Phe Arg Asn Ser Asp Arg Ile Leu Tyr Ser Ser Asp Trp Leu Ile
        35                  40                  45

Tyr Lys Thr Thr Asp His Tyr Gln Thr Phe Thr Lys Ile Arg
        50                  55                  60

```
<210> SEQ ID NO 18
<211> LENGTH: 48
<212> TYPE: PRT
<213> ORGANISM: Bacillus amyloliquefaciens
<220> FEATURE:
<221> NAME/KEY: SITE
<222> LOCATION: (48)
```

```
<223> OTHER INFORMATION: wherein COSBn is benzyl thio ester

<400> SEQUENCE: 18

Ala Gln Val Ile Asn Thr Phe Asp Gly Val Ala Asp Tyr Leu Gln Thr
 1               5                  10                  15

Tyr His Lys Leu Pro Asn Asp Tyr Ile Thr Lys Ser Glu Ala Gln Ala
            20                  25                  30

Leu Gly Trp Val Ala Ser Lys Gly Asn Leu Ala Asp Val Ala Pro Gly
        35                  40                  45

<210> SEQ ID NO 19
<211> LENGTH: 48
<212> TYPE: PRT
<213> ORGANISM: Bacillus amyloliquefaciens
<220> FEATURE:
<221> NAME/KEY: SITE
<222> LOCATION: (48)
<223> OTHER INFORMATION: wherein COSPh is phenyl thio ester

<400> SEQUENCE: 19

Ala Gln Val Ile Asn Thr Phe Asp Gly Val Ala Asp Tyr Leu Gln Thr
 1               5                  10                  15

Tyr His Lys Leu Pro Asn Asp Tyr Ile Thr Lys Ser Glu Ala Gln Ala
            20                  25                  30

Leu Gly Trp Val Ala Ser Lys Gly Asn Leu Ala Asp Val Ala Pro Gly
        35                  40                  45

<210> SEQ ID NO 20
<211> LENGTH: 110
<212> TYPE: PRT
<213> ORGANISM: Bacillus amyloliquefaciens

<400> SEQUENCE: 20

Ala Gln Val Ile Asn Thr Phe Asp Gly Val Ala Asp Tyr Leu Gln Thr
 1               5                  10                  15

Tyr His Lys Leu Pro Asn Asp Tyr Ile Thr Lys Ser Glu Ala Gln Ala
            20                  25                  30

Leu Gly Trp Val Ala Ser Lys Gly Asn Leu Ala Asp Val Ala Pro Gly
        35                  40                  45

Cys Ser Ile Gly Gly Asp Ile Phe Ser Asn Arg Glu Gly Lys Leu Pro
        50                  55                  60

Gly Lys Ser Gly Arg Thr Trp Arg Glu Ala Asp Ile Asn Tyr Thr Ser
65                  70                  75                  80

Gly Phe Arg Asn Ser Asp Arg Ile Leu Tyr Ser Ser Asp Trp Leu Ile
                85                  90                  95

Tyr Lys Thr Thr Asp His Tyr Gln Thr Phe Thr Lys Ile Arg
                100                 105                 110
```